United States Patent
Kokkoli et al.

(10) Patent No.: US 10,415,040 B2
(45) Date of Patent: Sep. 17, 2019

(54) NUCLEIC ACID AMPHIPHILES AND NANOSTRUCTURES

(71) Applicant: REGENTS OF THE UNIVERSITY OF MINNESOTA, Minneapolis, MN (US)

(72) Inventors: Efrosini Kokkoli, Minneapolis, MN (US); Timothy R. Pearce, Minneapolis, MN (US); Huihui Kuang, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 15/321,644

(22) PCT Filed: Jun. 22, 2015

(86) PCT No.: PCT/US2015/037005
§ 371 (c)(1),
(2) Date: Dec. 22, 2016

(87) PCT Pub. No.: WO2015/200220
PCT Pub. Date: Dec. 30, 2015

(65) Prior Publication Data
US 2017/0218367 A1  Aug. 3, 2017

Related U.S. Application Data

(60) Provisional application No. 62/016,045, filed on Jun. 23, 2014.

(51) Int. Cl.
  *C12N 15/113* (2010.01)
  *B82Y 5/00* (2011.01)
  *C12N 15/115* (2010.01)
  *A61K 47/69* (2017.01)
  *A61K 9/00* (2006.01)
  *A61K 47/26* (2006.01)
  (Continued)

(52) U.S. Cl.
  CPC .......... *C12N 15/115* (2013.01); *A61K 9/0092* (2013.01); *A61K 47/26* (2013.01); *A61K 47/6925* (2017.08); *B82Y 5/00* (2013.01); *B82Y 30/00* (2013.01); *B82Y 40/00* (2013.01); *C12N 2310/16* (2013.01); *C12N 2310/3515* (2013.01)

(58) Field of Classification Search
None
See application file for complete search history.

(56) References Cited

U.S. PATENT DOCUMENTS 8,246,995 B2 * 8/2012 Dai .................. B82Y 5/00
  423/447.1
2013/0123347 A1 * 5/2013 Kokkoli ............... C12N 15/115
  514/44 R

OTHER PUBLICATIONS

Hartgerink et al., Self-Assembly and Mineralization of Peptide-Amphiphile Nanofibers. Science, 2001, 294:1684-1688 (Year: 2001).*

(Continued)

*Primary Examiner* — Kevin K Hill
*Assistant Examiner* — Arthur S Leonard
(74) *Attorney, Agent, or Firm* — Viksnins Harris Padys Malen LLP

(57) ABSTRACT

Provided herein are nucleic acid amphiphiles and nanostructures such as nanotubes twisted nanotapes and helical nanotapes that comprise the amphiphiles as well as methods to deliver therapeutic agents with the nanostructures.

11 Claims, 13 Drawing Sheets

Specification includes a Sequence Listing.

(51) Int. Cl.
    B82Y 30/00     (2011.01)
    B82Y 40/00     (2011.01)

(56)            References Cited

OTHER PUBLICATIONS

Aldaye, et al., "Assembling materials with DNA as the guide", Science 321(5897), 1795-1799 (2008).
Chien, et al., "Programmable shape-shifting micelles", Angew Chem Int Ed Engl. 49(30), 5076-5080 (2010).
Kwak, et al., "Nucleic acid amphiphiles: synthesis and self-assembled nanostructures", Chem Soc Rev. 40(12), 5745-5755 (2011).
Lin, et al., "DNA tile based self-assembly: building complex nanoarchitectures", Chemphyschem. 7(8), 1641-1647 (2006).
Patent Cooperation Treaty, International Searching Authority, Search Report and Written Opinion for PCT/US2015/37005, 10 pages, dated Oct. 15, 2015.

Patwa, et al., "Hybrid lipid oligonucleotide conjugates: synthesis, self-assemblies and biomedical applications", Chem Soc Rev. 40(12), 5844-5854 (2011).
Pearce, et al., "DNA nanotubes and helical nanotapes via self-assembly of ssDNA-amphiphilest", Soft Matter, 1-3 (2014).
Pearce, et al., "The role of spacers on the self-assembly of DNA aptamer-amphiphiles into micelles and nanotapes", Chem Commun 50(2), 210-212 (2014).
Pinheiro, et al., "Challenges and opportunities for structural DNA nanotechnology", Nat Nanotechnol 6 (12), 763-772 (2011).
Seeman, et al., "Nanomaterials based on DNA", Annu Rev Biochem. 79, 65-87 (2010).
Torring, et al., "DNA origami: a quantum leap for self-assembly of complex structures", Chem Soc Rev. 40(12), 5636-46 (2011).
Waybrant, "Effect of polyethylene glycol, alkyl, and oligonucleotide spacers on the binding, secondary structure, and self-assembly of fractalkine binding FKN-S2 aptamer-amphiphiles", Langmuir 30(25), 7465-7474 (2014).
Wilner, et al., "Self-assembly of DNA nanotubes with controllable diameters", Nature Communications 2 (540), doi:10.1038/ncomms 1535, Abstract (2011).

* cited by examiner

Figure 7

|  |  | No Spacer | | $C_{12}$ Spacer | |
|---|---|---|---|---|---|
|  |  | Expected Mass (M-H) | Observed Mass (M-H) | Expected Mass (M-H) | Observed Mass (M-H) |
| No G Headgroups | 10nt-1 | 3,801.1 | 3,799.6 | 3,998.5 | 3,997.1 |
|  | 10nt-2 | 3,834.2 | 3,832.6 | 4,031.6 | 4,030.0 |
|  | 25nt | 8,364.1 | 8,361.7 | 8,561.5 | 8,559.4 |
|  | 40nt | 12,930.1 | 12,927.2 | 13,127.5 | 13,127.5 |
| $G_5$ Headgroups | 10nt-1 | 3,932.2 | 3,930.9 | 4,129.6 | 4,128.3 |
|  | 10nt-2 | 3,980.2 | 3,979.4 | 4,177.6 | 4,176.3 |
|  | 25nt | 8,495.2 | 8,493.0 | 8,692.6 | 8,690.0 |
|  | 40nt | 13,061.1 | 13,058.5 | 13,258.5 | 13,255.3 |
| $(GGGT)_3$ Headgroups | 25nt | 8,631.2 | 8,630.9 |  |  |
|  | 40nt | 13,197.2 | 13,196.9 |  |  |

NUCLEIC ACID AMPHIPHILES AND NANOSTRUCTURES

CROSS-REFERENCE TO RELATED APPLICATION

This patent application claims the benefit of priority of U.S. application Ser. No. 62/016,045, filed Jun. 23, 2014, which application is herein incorporated by reference.

STATEMENT OF GOVERNMENT SUPPORT

This invention was made with government support under NSF/CBET-0846274 awarded by the National Science Foundation. The government has certain rights in the invention.

SEQUENCE LISTING

The instant application contains a Sequence Listing which has been submitted electronically in ASCII format and is hereby incorporated by reference in its entirety. Said ASCII copy, created on Jul. 24, 2015, is named 09532_393US1_SL.txt and is 4,046 bytes in size.

BACKGROUND OF INVENTION

The field of DNA nanotechnology has transformed DNA from a biological material that stores genetic information into a construction material that can be used to build 3-dimensional scaffolds, structures, and devices with nanoscale features (N. C. Seeman, *Annu. Rev. Biochem.*, 2010, 79, 65-87; A. V. Pinheiro, et al., *Nat. Nanotechnol.* 2011, 6, 763-772). The ability to precisely control the organization of DNA relies on Watson-Crick base pairing, which acts as a molecular glue to hold strands of DNA together in a predictable manner. There are a variety of strategies that can be used to create DNA nanostructures, each that use a combination of different single-stranded (ssDNA) sequences that when mixed together and subjected to specific annealing conditions (i.e., controlled cooling rates, specific ions, and pH) fold together to produce double stranded DNA segments that organize into highly uniform structures of the desired shape (T. Toning, et al., Gothelf, *Chem. Soc. Rev.*, 2011, 40, 5636-5646; C. Lin, et al., *ChemPhysChem*, 2006, 7, 1641-1647; F. A. Aldaye, et al., *Science*, 2008, 321, 1795-1799). The predictability of base pairing affords the opportunity to rationally select these ssDNA sequences, often with the aid of software, that can combine together to form tetrahedrons, cages, barrels, and tube structures while maintaining ssDNA overhangs that act as addressable locations and allow the structures to be further functionalized with drugs, dyes, and metals for use as therapeutics, diagnostics, electronics and photonics, and in molecular and cellular biophysical studies (A. V. Pinheiro, et al., *Nat. Nanotechnol.* 2011, 6, 763-772; F. A. Aldaye, et al., *Science*, 2008, 321, 1795-1799).

An alternative approach to form DNA nanostructures is to covalently link a hydrophilic ssDNA sequence with a hydrophobic tail (a polymer or other hydrophobic moiety) to form an amphiphilic molecule (e.g., a nucleic acid amphiphile) (M. Kwak, et al., *Chem. Soc. Rev.*, 2011, 40, 5745-5755; A. Patwa, et al., *Chem. Soc. Rev.*, 2011, 40, 5844-5854). The amphiphilic nature of the conjugate induces spontaneous assembly of the molecules when added to an aqueous environment, with the hydrophobic tails preferring to sequester themselves into a hydrophobic domain while the ssDNA sequences extend into the aqueous solution. With this structural arrangement the ssDNA is not required to base pair in order to create the nanostructure and remains available for base pairing with complimentary ssDNA sequences. Additionally, this approach to forming DNA nanostructures does not require base pairing prediction software and reduces the requirements for specific annealing conditions. However, this approach has not yet been used to create nanostructures with similar levels of complexity as those achieved by other approaches like DNA origami and DNA tile assembly (F. A. Aldaye, et al., *Science*, 2008, 321, 1795-1799). To date, the majority of structures created by ssDNA-amphiphile assembly have been spherical and cylindrical micelles (M. Kwak, et al., *Chem. Soc. Rev.*, 2011, 40, 5745-5755; M.-P. Chien, et al., *Angew. Chem. Int. Ed.*, 2010, 49, 5076-5080).

Another study investigated how an additional building block, a spacer molecule used to link a ssDNA aptamer headgroup and hydrophobic lipid-like tail, could affect ssDNA-amphiphile assembly (T. R. Pearce, et al., *Chem. Commun.*, 2014, 50, 210-212). It was found that globular micelles were formed when a 25 nucleotide aptamer was directly conjugated to a $C_{16}$ dialkyl tail or conjugated to the tail via hydrophilic $PEG_4$ or $PEG_8$ spacers, but that flat and twisted nanotapes comprised of bilayers of amphiphiles were formed when hydrophobic $C_{12}$ and $C_{24}$ spacers were used (T. R. Pearce, et al., *Chem. Commun.*, 2014, 50, 210-212). The nanotape morphology achieved by including a hydrophobic spacer in the design of the amphiphile was not predicted by the standard packing parameter analysis, leading to the hypothesis that polycarbon spacers, through attractive hydrophobic interactions, may force the aptamer headgroups into close proximity of each other, thus reducing the interfacial headgroup area and allowing the nanotapes to form (T. R. Pearce, et al., *Chem. Commun.*, 2014, 50, 210-212). Other studies have shown that amphiphiles created with a 40 nucleotide ssDNA aptamer headgroup containing a large number of guanine nucleotides capable of forming intermolecular parallel G-quadruplexes with neighbouring aptamer headgroups self-assembled into nanotapes in the absence of a polycarbon spacer (B. Waybrant, et al., *Langmuir*, 2014, DOI: 10.1021/la500403v). This finding suggested that the intermolecular interactions that produced the G-quadruplex structure may have reduced the effective headgroup area of the ssDNA in a manner analogous to the polycarbon spacer and encouraged the assembly of bilayer nanotapes (B. Waybrant, et al., *Langmuir*, 2014, DOI: 10.1021/la500403v). Thus, the factors that influence assembly of ssDNA-amphiphiles into 3-dimensional structures is complex.

There is an ongoing need for 3-dimensional structures with nano-scale features (e.g., nanotubes, twisted nanotapes or helical nanotapes) including ones that are based on nucleic acid amphiphiles (e.g., ssDNA amphiphiles). There is also a need for 3-dimensional structures with nano-scale features (e.g., nanotubes, twisted nanotapes or helical nanotapes formed from ssDNA amphiphiles) that can be used, for example, to deliver therapeutic agents and/or target certain biological molecules and/or detect certain proteins or as templates for the design and engineering of other materials.

SUMMARY OF THE INVENTION

One embodiment provides a nanostructure (e.g., a nanotube, twisted nanotape or helical nanotape) comprising a nucleic acid amphiphile of formula I:

A-B-C-D            I wherein:

A is a saturated or unsaturated ($C_{10}$-$C_{150}$) hydrocarbon chain wherein one or more of the carbon atoms of the hydrocarbon chain is optionally replaced independently with an —O—, —S—, N or —NR— group and wherein one or more of the carbon atoms of the hydrocarbon chain is optionally substituted independently with an oxo or thioxo group, and wherein each R is independently an H, saturated ($C_1$-$C_{10}$) hydrocarbon chain or unsaturated ($C_2$-$C_{10}$) hydrocarbon chain;

B is absent, or B is a spacer group wherein the spacer group is a saturated or unsaturated ($C_5$-$C_{50}$) hydrocarbon chain wherein one or more of the carbon atoms of the hydrocarbon chain is optionally replaced independently with an O, S or NR group and wherein one or more of the carbon atoms of the hydrocarbon chain is optionally substituted independently with an oxo or thioxo group, and wherein each R is independently H, saturated ($C_1$-$C_{10}$) hydrocarbon chain or unsaturated ($C_2$-$C_{10}$) hydrocarbon chain;

C is absent, or C is a linker group wherein the linker group is a saturated or unsaturated ($C_2$-$C_{10}$) hydrocarbon chain wherein one or more of the carbon atoms of the hydrocarbon chain is optionally replaced independently with an —O—, —S— or —NR— group and wherein one or more of the carbon atoms of the hydrocarbon chain is optionally substituted independently with an oxo, thioxo or hydoxyl group, and wherein each R is independently H, saturated ($C_1$-$C_{10}$) hydrocarbon chain or unsaturated ($C_2$-$C_{10}$) hydrocarbon chain; and D is a polynucleotide;

or a salt thereof.

One embodiment provides a nucleic acid amphiphile of formula I:

A-B-C-D            I wherein:

A is a saturated or unsaturated ($C_{10}$-$C_{150}$) hydrocarbon chain wherein one or more of the carbon atoms of the hydrocarbon chain is optionally replaced independently with an —O—, —S—, N or —NR— group and wherein one or more of the carbon atoms of the hydrocarbon chain is optionally substituted independently with an oxo or thioxo group, and wherein each R is independently an H, saturated ($C_1$-$C_{10}$) hydrocarbon chain or unsaturated ($C_2$-$C_{10}$) hydrocarbon chain;

B is absent, or B is a spacer group wherein the spacer group is a saturated or unsaturated ($C_5$-$C_{50}$) hydrocarbon chain wherein one or more of the carbon atoms of the hydrocarbon chain is optionally replaced independently with an —O—, —S or —NR— group and wherein one or more of the carbon atoms of the hydrocarbon chain is optionally substituted independently with an oxo or thioxo group, and wherein each R is independently H, saturated ($C_1$-$C_{10}$) hydrocarbon chain or unsaturated ($C_2$-$C_{10}$) hydrocarbon chain;

C is absent, or C is a linker group wherein the linker group is a saturated or unsaturated ($C_2$-$C_{10}$) hydrocarbon chain wherein one or more of the carbon atoms of the hydrocarbon chain is optionally replaced independently with an —O—, —S or —NR— group and wherein one or more of the carbon atoms of the hydrocarbon chain is optionally substituted independently with an oxo, thioxo or hydoxyl group, and wherein each R is independently H, saturated ($C_1$-$C_{10}$) hydrocarbon chain or unsaturated ($C_2$-$C_{10}$) hydrocarbon chain; and D is a polynucleotide;

or a salt thereof.

One embodiment provides a pharmaceutical composition comprising a nanotube as described herein or a pharmaceutically acceptable salt thereof and a pharmaceuticaly acceptable carrier.

One embodiment provides a nanotube as described herein or a pharmaceutically acceptable salt thereof for use in medical therapy.

BRIEF DESCRIPTION OF THE FIGURES

FIG. 1A discloses SEQ ID NOS 4-7, 3 and 8-12, respectively, in order of appearance.

FIG. 7 shows the LC-MS data of the 10, 25, and 40 nucleotide (nt) ssDNA-amphiphiles created with and without a $C_{12}$ spacer and various headgroups, as shown in FIG. 1. FIG. 7 discloses '$(GGGT)_3$' as SEQ ID NO: 1.

DETAILED DESCRIPTION

Figure 1:
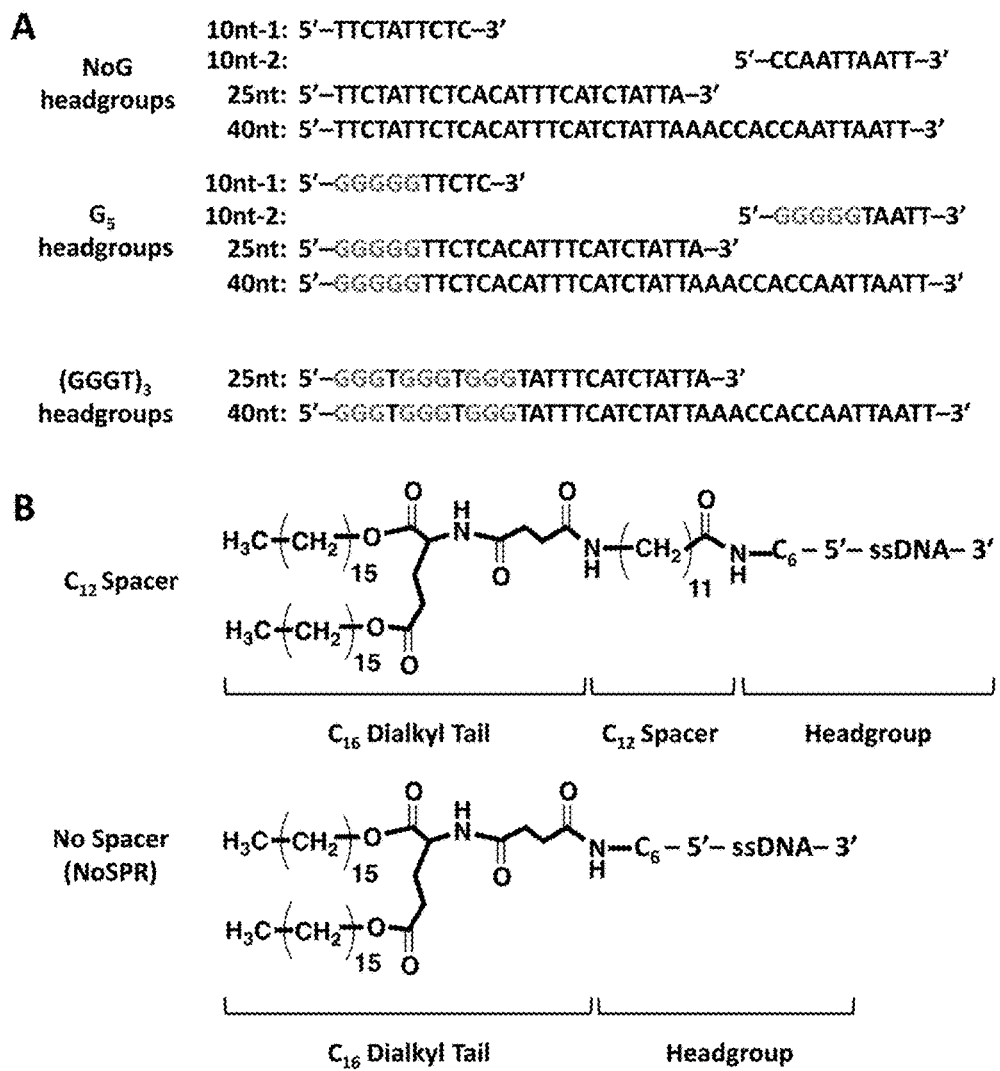
FIG. 1A illustrates sequences of the 10 nucleotide (nt), 25 nucleotide, and 40 nucleotide guanine-free (NoG) and guanine-modified headgroups (having either a $G_5$ or a $(GGGT)_3$ (SEQ ID NO: 1) sequence) used to create the ssDNA-amphiphiles
FIG. 1B illustrates chemical structures of ssDNA-amphiphiles with a $C_{16}$ dialkyl tail, a $C_{12}$ spacer or without a spacer (NoSPR), and a ssDNA headgroup containing a $C_6$ linker and having different sequences as shown in A.

The nanostructures (e.g., nanotubes, twisted nanotapes and helical nanotapes) described herein are generally formed via the self-assembly of nucleic acid amphiphiles (e.g., ssDNA-amphiphiles). The nucleic acid amphiphiles as used herein refers to an amphiphile comprising a hydrophilic headgroup (e.g., polynucleotide) which is generally a single stranded polynucleotide segment that is covalently bonded to a hydrophobic (lipophilic) group or tail (e.g., hydrocarbon chain). In one embodiment the polynucleotide headgroup is separated from the hydrophobic group by a spacer and/or a linker.

The term "saturated hydrocarbon chain" as used herein refers to a straight or branched chain of the specified number of carbon atoms that is saturated. It is to be understood that a branched chain can have multiple braches (e.g., 1, 2, 3, 4 or more)

The term "unsaturated hydrocarbon chain" as used herein refers to a straight or branched chain of the specified number of carbon atoms that has one or more carbon-carbon double bonds or carbon-carbon triple bonds or a combination thereof. It is to be understood that a branched chain can have multiple braches (e.g., 1, 2, 3, 4 or more)

The term "oxo" as used herein is an "=O" group

The term "thioxo" as used herein is an "=S" group

Polynucleotide

The polynucleotides that make up the hydrophilic headgroup of the nucleic acid amphiphiles are single stranded polynucleotides. The nucleotides contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines. The polynucleotide can contain any single stranded nucleic acid (e.g., ssDNA) sequence or mixture of sequences and can of variable length. In one embodiment the polynucleotide comprises 5-50 nucleotides. In one embodiment the polynucleotide comprises 5-100 nucleotides. In one embodiment the polynucleotide comprises 5-200 nucleotides. In one embodiment the polynucleotide comprises 2-50 nucleotides. In one embodiment the polynucleotide comprises 2-100 nucleotides.

The polynucleotide segment can be connected to the "spacer (B)" or the "hydrophobic group (A)" at the 3' or 5' end of the polynucleotide. In one embodiment the polynucleotides can be connected to the "spacer" or the "hydrophobic tail" through the oxygen atom of the 3' or 5' phosphate. In one embodiment the polynucleotides can be connected to the "spacer" or the "hydrophobic tail" through the oxygen atom of the 5' phosphate. In one embodiment the polynucleotides can be connected to the "spacer" or the "hydrophobic tail" through the oxygen atom of the 3' phosphate. In one embodiment the polynucleotides can be connected to the "spacer" or the "hydrophobic tail" through the oxygen atom of the sugar ring at the 3' position. The polynucleotides can also be connected to the "spacer" or the "hydrophobic tail" at an internal nucleotide of the polynucleotide.

The polynucleotide segment can be also connected to the "spacer (B)" or the "hydrophobic group (A)" at the 3' or 5' end of the polynucleotide through a linker (C). In one embodiment the polynucleotides can be connected to the "spacer" or the "hydrophobic tail" through a linker that is bonded to the oxygen atom of the 3' or 5' phosphate. In one embodiment the polynucleotides can be connected to the "spacer" or the "hydrophobic tail" through a linker that is bonded to the oxygen atom of the 5' phosphate. In one embodiment the polynucleotides can be connected to the "spacer" or the "hydrophobic tail" through a linker that is bonded to the oxygen atom of the 3' phosphate. In one embodiment the polynucleotides can be connected to the "spacer" or the "hydrophobic tail" through a linker that is bonded to the oxygen atom of the sugar ring at the 3' position.

The polynucleotides can also be connected to the "linker" at an internal nucleotide of the polynucleotide.

Polynucleotides may be modified. Such modifications may be useful to increase stability of the polynucleotide in certain environments. Modifications can include modifications to the nucleic acid sugar, the base or backbone or any combination thereof. The modifications can be synthetic, naturally occurring, or non-naturally occurring. A polynucleotide can include modifications at one or more of the nucleic acids present in the polynucleotide.

Polynucleotides can be produced in vitro or in vivo. For instance, methods for in vitro synthesis include, but are not limited to chemical synthesis with a conventional DNA/RNA synthesizer. Commercial suppliers of synthetic polynucleotides and reagents for in vitro synthesis are well known. Methods for in vitro synthesis also include, for instance, in vitro transcription using a circular or linear expression vector in a cell free system.

Hydrophobic group or hydrophobic tail

The hydrophobic group (A) or tail segment of the nucleic acid amphiphile is lipophilic in nature. In general the hydrophobic group includes hydrocarbon chains that are connected to the "spacer" or "polynucleotide headgroup" via functional groups such as but not limited to amide, ester, thioamide and thioester groups. In one embodiment the hydrophobic group is a saturated or unsaturated ($C_{10}$-$C_{150}$) hydrocarbon chain wherein one or more of the carbon atoms of the hydrocarbon chain is optionally replaced independently with an —O—, —S— or —NR— group and wherein one or more of the carbon atoms of the hydrocarbon chain is optionally substituted independently with an oxo or thioxo group, and wherein each R is independently an H, saturated ($C_1$-$C_{10}$) hydrocarbon chain or unsaturated ($C_2$-$C_{10}$) hydrocarbon chain. In one embodiment the hydrophobic group is a saturated or unsaturated ($C_{10}$-$C_{150}$) hydrocarbon chain wherein one or more of the carbon atoms of the hydrocarbon chain is replaced independently with an —O—, —S— or —NR— group and wherein one or more of the carbon atoms of the hydrocarbon chain is optionally substituted independently with an oxo or thioxo group, and wherein each R is independently an H, saturated ($C_1$-$C_{10}$) hydrocarbon chain or unsaturated ($C_2$-$C_{10}$) hydrocarbon chain. In one embodiment the hydrophobic group is a saturated or unsaturated ($C_{10}$-$C_{150}$) hydrocarbon chain wherein one or more of the carbon atoms of the hydrocarbon chain is optionally replaced independently with an —O—, —S or —NR— group and wherein one or more of the carbon atoms of the hydrocarbon chain is substituted independently with an oxo or thioxo group, and wherein each R is independently an H, saturated ($C_1$-$C_{10}$) hydrocarbon chain or unsaturated ($C_2$-$C_{10}$) hydrocarbon chain. In one embodiment the hydrophobic group is a saturated or unsaturated ($C_{10}$-$C_{150}$) hydrocarbon chain wherein one or more of the carbon atoms of the hydrocarbon chain is replaced independently with an —O—, —S or —NR— group and wherein one or more of the carbon atoms of the hydrocarbon chain is substituted independently with an oxo or thioxo group, and wherein each R is independently an H, saturated ($C_1$-$C_{10}$) hydrocarbon chain or unsaturated ($C_2$-$C_{10}$) hydrocarbon chain.

Spacer

The "spacer" group (B), if present separates the polynucleotide from the hydrophobic group. In one embodiment the spacer is hydrophobic. In one embodiment the spacer is a saturated or unsaturated ($C_5$-$C_{50}$) hydrocarbon chain wherein one or more of the carbon atoms of the hydrocarbon chain is optionally replaced independently with an —O—, —S or —NR— group and wherein one or more of the carbon atoms of the hydrocarbon chain is optionally substituted independently with an oxo or thioxo group, and wherein each R is independently H, saturated ($C_1$-$C_{10}$) hydrocarbon chain or unsaturated ($C_2$-$C_{10}$) hydrocarbon chain. In one embodiment the spacer is a saturated or unsaturated ($C_5$-$C_{50}$) hydrocarbon chain wherein one or more of the carbon atoms of the hydrocarbon chain is replaced independently with an —O—, —S or —NR— group and wherein one or more of the carbon atoms of the hydrocarbon chain is substituted independently with an oxo or thioxo group, and wherein each R is independently H, saturated ($C_1$-$C_{10}$) hydrocarbon chain or unsaturated ($C_2$-$C_{10}$) hydrocarbon chain.

Linker

The "linker" group (C), if present separates the polynucleotide from the spacer group or hydrophobic group. In one embodiment the linker is attached to the oxygen of the 5' phosphate of the polynucleotide. In one embodiment the linker is attached to the oxygen of the 3' phosphate of the polynucleotide. In one embodiment the linker is attached to the oxygen of the 3' phosphate of the polynucleotide or the 5' phosphate of the polynucleotide. The linker can be any combination of functional groups and hydrocarbon chains either alone or in combination. The linker may be a synthetic handle for which to join the polynucleotide to the spacer or hydrophobic group of the amphiphile. In one embodiment the linker group is a saturated or unsaturated ($C_2$-$C_{10}$) hydrocarbon chain wherein one of the carbon atoms of the hydrocarbon chain is optionally replaced with an —O—, —S— or —NR— group and wherein one of the carbon atoms of the hydrocarbon chain is optionally substituted with an oxo or thioxo group, and wherein each R is independently H, saturated ($C_1$-$C_{10}$) hydrocarbon chain or unsaturated ($C_2$-$C_{10}$) hydrocarbon chain.

It is to be understood that a saturated or unsaturated hydrocarbon chain wherein one or more of the carbon atoms of the hydrocarbon chain is optionally replaced independently with an —O—, —S or —NR— group and wherein one or more of the carbon atoms of the hydrocarbon chain is optionally substituted independently with an oxo or thioxo group provides certain functional groups, for example, but not limited to amides (—C(=O)NR—), esters (—C(=O)O—), ureas (—NRC(=O)NR—), carbonates (—OC(=O)O—), carbamates (—OC(=O)NR—) and all thioxo and —S— variants thereof. These groups are the result of the one or more carbons being replaced by a group selected from —O—, —S or —NR— and one or more adjacent carbons being substituted with an oxo or thioxo group. In one embodiment no —O—, —S or —NR— can be adjacent to another —O—, —S or —NR— group.

Embodiments

It is to be understood that one or more of the following embodiments may be combined and that the embodiments are for amphiphiles of formula I (nanostructures and amphiphiles) and all subformulas of formula I (e.g., formula Ia, Ib, Ic).

One embodiment provides a nanostructure (e.g., a nanotube, twisted nanotape or helical nanotape) comprising a nucleic acid amphiphile of formula I which is a compound of formula Ia:

A-D      Ia or a salt thereof.

One embodiment provides a nanostructure (e.g., a nanotube, twisted nanotape or helical nanotape) comprising a nucleic acid amphiphile of formula I which is a compound of formula Ib:

A-B-D      Ib or a salt thereof.

One embodiment provides a nanostructure (e.g., a nanotube, twisted nanotape or helical nanotape) comprising a nucleic acid amphiphile of formula I which is a compound of formula Ic:

A-C-D      Ic or a salt thereof.

One embodiment provides a nucleic acid amphiphile of formula I which is a compound of formula Ia:

A-D      Ia or a salt thereof.

One embodiment provides a nucleic acid amphiphile of formula I which is a compound of formula Ib:

A-B-D      Ib or a salt thereof.

One embodiment provides a nucleic acid amphiphile of formula I which is a compound of formula Ic:

A-C-D      Ic or a salt thereof.

One embodiment provides a nanostructure (e.g., a nanotube, twisted nanotape or helical nanotape) comprising a nucleic acid amphiphile of formula I:

A-B-C-D      I wherein:

A is a saturated or unsaturated ($C_{10}$-$C_{150}$) hydrocarbon chain wherein one or more of the carbon atoms of the hydrocarbon chain is optionally replaced independently with an —O—, —S or —NR— group and wherein one or more of the carbon atoms of the hydrocarbon chain is optionally substituted independently with an oxo or thioxo group, and wherein each R is independently an H, saturated ($C_1$-$C_{10}$) hydrocarbon chain or unsaturated ($C_2$-$C_{10}$) hydrocarbon chain;

B is absent, or B is a spacer group wherein the spacer group is a saturated or unsaturated ($C_5$-$C_{50}$) hydrocarbon chain wherein one or more of the carbon atoms of the hydrocarbon chain is optionally replaced independently with an O, S or NR group and wherein one or more of the carbon atoms of the hydrocarbon chain is optionally substituted independently with an oxo or thioxo group, and wherein each R is independently H, saturated ($C_1$-$C_{10}$) hydrocarbon chain or unsaturated ($C_2$-$C_{10}$) hydrocarbon chain;

C is absent or C is a linker group wherein the linker group is a saturated or unsaturated ($C_2$-$C_{10}$) hydrocarbon chain wherein one of the carbon atoms of the hydrocarbon chain is optionally replaced with an O, S or NR group and wherein one of the carbon atoms of the hydrocarbon is optionally substituted with an oxo or thioxo group, and wherein each R is independently H, saturated ($C_1$-$C_{10}$) hydrocarbon chain or unsaturated ($C_2$-$C_{10}$) hydrocarbon chain; and D is a polynucleotide;

or a salt thereof.

One embodiment provides a nucleic acid amphiphile of formula I:

A-B-C-D    I wherein:

A is a saturated or unsaturated ($C_{10}$-$C_{150}$) hydrocarbon chain wherein one or more of the carbon atoms of the hydrocarbon chain is optionally replaced independently with an —O—, —S or —NR— group and wherein one or more of the carbon atoms of the hydrocarbon chain is optionally substituted independently with an oxo or thioxo group, and wherein each R is independently an H, saturated ($C_1$-$C_{10}$) hydrocarbon chain or unsaturated ($C_2$-$C_{10}$) hydrocarbon chain;

B is absent, or B is a spacer group wherein the spacer group is a saturated or unsaturated ($C_5$-$C_{50}$) hydrocarbon chain wherein one or more of the carbon atoms of the hydrocarbon chain is optionally replaced independently with an —O—, —S or —NR— group and wherein one or more of the carbon atoms of the hydrocarbon chain is optionally substituted independently with an oxo or thioxo group, and wherein each R is independently H, saturated ($C_1$-$C_{10}$) hydrocarbon chain or unsaturated ($C_2$-$C_{10}$) hydrocarbon chain;

C is absent or C is a linker group wherein the linker group is a saturated or unsaturated ($C_2$-$C_{10}$) hydrocarbon chain wherein one of the carbon atoms of the hydrocarbon chain is optionally replaced with an —O—, —S or —NR— group and wherein one of the carbon atoms of the hydrocarbon is optionally substituted with an oxo or thioxo group, and wherein each R is independently H, saturated ($C_1$-$C_{10}$) hydrocarbon chain or unsaturated ($C_2$-$C_{10}$) hydrocarbon chain; and D is a polynucleotide;

or a salt thereof.

In one embodiment A is a saturated or unsaturated ($C_{20}$-$C_{80}$) hydrocarbon chain wherein one or more of the carbon atoms of the hydrocarbon chain is optionally replaced independently with an —O—, —S or —NR— group and wherein one or more of the carbon atoms of the hydrocarbon chain is optionally substituted independently with an oxo or thioxo group, and wherein each R is independently an H, saturated ($C_1$-$C_{10}$) hydrocarbon or unsaturated ($C_2$-$C_{10}$) hydrocarbon chain.

In one embodiment A is a saturated or unsaturated ($C_{20}$-$C_{70}$) hydrocarbon chain wherein one or more of the carbon atoms of the hydrocarbon chain is optionally replaced independently with an —O—, —S or —NR— group and wherein one or more of the carbon atoms of the hydrocarbon is optionally substituted independently with an oxo or thioxo group, and wherein each R is independently H, saturated ($C_1$-$C_{10}$) hydrocarbon chain or unsaturated ($C_2$-$C_{10}$) hydrocarbon chain.

In one embodiment A is a saturated or unsaturated ($C_{30}$-$C_{70}$) hydrocarbon chain wherein one or more of the carbon atoms of the hydrocarbon chain is optionally replaced independently with an —O—, —S or —NR— group and wherein one or more of the carbon atoms of the hydrocarbon chain is optionally substituted independently with an oxo or thioxo group, and wherein each R is independently H, saturated ($C_1$-$C_{10}$) hydrocarbon chain or unsaturated ($C_2$-$C_{10}$) hydrocarbon chain.

In one embodiment A is a saturated or unsaturated ($C_{20}$-$C_{80}$) hydrocarbon chain wherein one or more of the carbon atoms of the hydrocarbon chain is replaced independently with an —O—, —S or —NR— group and wherein one or more of the carbon atoms of the hydrocarbon chain is optionally substituted independently with an oxo or thioxo group, and wherein each R is independently an H, saturated ($C_1$-$C_{10}$) hydrocarbon or unsaturated ($C_2$-$C_{10}$) hydrocarbon chain.

In one embodiment A is a saturated or unsaturated ($C_{20}$-$C_{70}$) hydrocarbon chain wherein one or more of the carbon atoms of the hydrocarbon chain is replaced independently with an —O—, —S or —NR— group and wherein one or more of the carbon atoms of the hydrocarbon is optionally substituted independently with an oxo or thioxo group, and wherein each R is independently H, saturated ($C_1$-$C_{10}$) hydrocarbon chain or unsaturated ($C_2$-$C_{10}$) hydrocarbon chain.

In one embodiment A is a saturated or unsaturated ($C_{30}$-$C_{70}$) hydrocarbon chain wherein one or more of the carbon atoms of the hydrocarbon chain is replaced independently with an —O—, —S or —NR— group and wherein one or more of the carbon atoms of the hydrocarbon chain is optionally substituted independently with an oxo or thioxo group, and wherein each R is independently H, saturated ($C_1$-$C_{10}$) hydrocarbon chain or unsaturated ($C_2$-$C_{10}$) hydrocarbon chain.

In one embodiment A is a saturated or unsaturated ($C_{20}$-$C_{80}$) hydrocarbon chain wherein one or more of the carbon atoms of the hydrocarbon chain is optionally replaced independently with an —O—, —S or —NR— group and wherein one or more of the carbon atoms of the hydrocarbon chain is substituted independently with an oxo or thioxo group, and wherein each R is independently an H, saturated ($C_1$-$C_{10}$) hydrocarbon or unsaturated ($C_2$-$C_{10}$) hydrocarbon chain.

In one embodiment A is a saturated or unsaturated ($C_{20}$-$C_{70}$) hydrocarbon chain wherein one or more of the carbon atoms of the hydrocarbon chain is optionally replaced independently with an —O—, —S or —NR— group and wherein one or more of the carbon atoms of the hydrocarbon is substituted independently with an oxo or thioxo group, and wherein each R is independently H, saturated ($C_1$-$C_{10}$) hydrocarbon chain or unsaturated ($C_2$-$C_{10}$) hydrocarbon chain.

In one embodiment A is a saturated or unsaturated ($C_{30}$-$C_{70}$) hydrocarbon chain wherein one or more of the carbon atoms of the hydrocarbon chain is optionally replaced independently with an —O—, —S or —NR— group and wherein one or more of the carbon atoms of the hydrocarbon chain is substituted independently with an oxo or thioxo group, and wherein each R is independently H, saturated ($C_1$-$C_{10}$) hydrocarbon chain or unsaturated ($C_2$-$C_{10}$) hydrocarbon chain.

In one embodiment A includes one or more saturated or unsaturated ($C_{10}$-$C_{22}$) hydrocarbon chain segments.

In one embodiment A includes 1, 2, 3 or 4 saturated or unsaturated ($C_{10}$-$C_{22}$) hydrocarbon chain segments.

In one embodiment A includes 1, 2 or 3 saturated or unsaturated ($C_{10}$-$C_{22}$) hydrocarbon chain segments.

In one embodiment A includes for 2 saturated or unsaturated ($C_{10}$-$C_{22}$) hydrocarbon chain segments.

In one embodiment A includes 1, 2 or 3 saturated ($C_{12}$-$C_{20}$) hydrocarbon chain segments.

In one embodiment A includes 1 or 2 saturated ($C_{12}$-$C_{20}$) hydrocarbon chain segments.

In one embodiment 1, 2, 3, 4, 5, 6, 7 or 8 of the carbon atoms of the hydrocarbon chain of A is replaced independently with an —O—, —S or —NR— group and wherein 1, 2, 3, 4, 5, 6, 7 or 8 of the carbon atoms of the hydrocarbon chain of A is substituted independently with an oxo or thioxo group, and wherein each R is independently an H, saturated ($C_1$-$C_{10}$) hydrocarbon chain or unsaturated ($C_2$-$C_{10}$) hydrocarbon chain.

In one embodiment 1, 2, 3, 4, 5 or 6 of the carbon atoms of the hydrocarbon chain of A is replaced independently with an —O—, —S or —NR— group and wherein 1, 2, 3, 4, 5 or 6 of the carbon atoms of the hydrocarbon chain of A substituted independently with an oxo or thioxo group, and wherein each R is independently an H, saturated ($C_1$-$C_{10}$) hydrocarbon chain or unsaturated ($C_2$-$C_{10}$) hydrocarbon chain.

In one embodiment A has the formula:

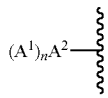

wherein:

each $A^1$ is independently a saturated or unsaturated ($C_5$-$C_{30}$) hydrocarbon chain;

$A^2$ is a saturated or unsaturated ($C_5$-$C_{25}$) hydrocarbon wherein one or more of the carbon atoms of the hydrocarbon is replaced independently with an —O—, —S or —NR— group and wherein one or more of the carbon atoms of the hydrocarbon is optionally substituted independently with an oxo or thioxo group, and wherein each R is independently an H, saturated ($C_1$-$C_{10}$) hydrocarbon chain or unsaturated ($C_2$-$C_{10}$) hydrocarbon chain; and n is 1, 2, 3 or 4.

It is to be understood that each A1 can be connected to A2 at any atom of A2 (provided that the atom has the open valence to allow for the bonding of A1 to A2)

In one embodiment each $A^1$ is independently a saturated or unsaturated ($C_{10}$-$C_{30}$) hydrocarbon chain.

In one embodiment each $A^1$ is independently a saturated ($C_{10}$-$C_{30}$) hydrocarbon chain.

In one embodiment each $A^1$ is independently a saturated ($C_{10}$-$C_{25}$) hydrocarbon chain.

In one embodiment A has the formula:

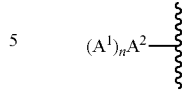

wherein:

each $A^1$ is independently a saturated or unsaturated ($C_5$-$C_{30}$) hydrocarbon chain wherein one or more of the carbon atoms of the hydrocarbon is replaced independently with an —O—, —S or —NR— group and wherein one or more of the carbon atoms of the hydrocarbon is optionally substituted independently with an oxo or thioxo group, and wherein each R is independently an H, saturated ($C_1$-$C_{10}$) hydrocarbon chain or unsaturated ($C_2$-$C_{10}$) hydrocarbon chain; and $A^2$ is a saturated or unsaturated ($C_5$-$C_{25}$) hydrocarbon wherein one or more of the carbon atoms of the hydrocarbon is replaced independently with an —O—, —S or —NR— group and wherein one or more of the carbon atoms of the hydrocarbon is optionally substituted independently with an oxo or thioxo group, and wherein each R is independently an H, saturated ($C_1$-$C_{10}$) hydrocarbon chain or unsaturated ($C_2$-$C_{10}$) hydrocarbon chain; and n is 1, 2, 3 or 4.

In one embodiment each $A^1$ is independently a saturated or unsaturated ($C_{10}$-$C_{30}$) hydrocarbon chain wherein one or more of the carbon atoms of the hydrocarbon is replaced independently with an —O—, —S or —NR— group and wherein one or more of the carbon atoms of the hydrocarbon is optionally substituted independently with an oxo or thioxo group, and wherein each R is independently an H, saturated ($C_1$-$C_{10}$) hydrocarbon chain or unsaturated ($C_2$-$C_{10}$) hydrocarbon chain.

In one embodiment each $A^1$ is independently a saturated ($C_{10}$-$C_{30}$) hydrocarbon chain wherein one or more of the carbon atoms of the hydrocarbon is replaced independently with an —O—, —S or —NR— group and wherein one or more of the carbon atoms of the hydrocarbon is optionally substituted independently with an oxo or thioxo group, and wherein each R is independently an H, saturated ($C_1$-$C_{10}$) hydrocarbon chain or unsaturated ($C_2$-$C_{10}$) hydrocarbon chain.

In one embodiment each $A^1$ is independently a saturated ($C_{10}$-$C_{25}$) hydrocarbon chain wherein one or more of the carbon atoms of the hydrocarbon is replaced independently with an —O—, —S or —NR— group and wherein one or more of the carbon atoms of the hydrocarbon is optionally substituted independently with an oxo or thioxo group, and wherein each R is independently an H, saturated ($C_1$-$C_{10}$) hydrocarbon chain or unsaturated ($C_2$-$C_{10}$) hydrocarbon chain.

In one embodiment n is 1, 2 or 3.

In one embodiment n is 1 or 2.

In one embodiment $A^2$ is saturated or unsaturated ($C_{10}$-$C_{20}$) hydrocarbon wherein one or more of the carbon atoms of the hydrocarbon chain is replaced independently with an —O—, —S or —NR— group and wherein one or more of the carbon atoms of the hydrocarbon is optionally substituted independently with an oxo or thioxo group, and wherein each R is independently an H, saturated ($C_1$-$C_{10}$) hydrocarbon chain or unsaturated ($C_2$-$C_{10}$) hydrocarbon chain.

In one embodiment $A^2$ is saturated ($C_{10}$-$C_{20}$) hydrocarbon wherein 1, 2, 3, 4, 5, 6, 7 or 8 of the carbon atoms of the hydrocarbon chain is replaced independently with an —O—, —S or —NR— group and wherein 1, 2, 3, 4, 5, 6, 7 or 8 of the carbon atoms of the hydrocarbon is substituted independently with an oxo or thioxo group, and wherein each R is independently an H, saturated ($C_1$-$C_{10}$) hydrocarbon chain or unsaturated ($C_2$-$C_{10}$) hydrocarbon chain.

In one embodiment $A^2$ is saturated ($C_{10}$-$C_{16}$) hydrocarbon wherein 1, 2, 3, 4, 5 or 6 of the carbon atoms of the hydrocarbon chain is replaced independently with an —O—, —S or —NR— group and wherein 1, 2, 3, 4, 5 or 6 of the carbon atoms of the hydrocarbon chain is substituted independently with an oxo or thioxo group, and wherein each R is independently an H, saturated ($C_1$-$C_{10}$) hydrocarbon chain or unsaturated ($C_2$-$C_{10}$) hydrocarbon chain.

In one embodiment $A^2$ is saturated ($C_{10}$-$C_{16}$) hydrocarbon wherein 1, 2, 3, 4, 5 or 6 of the carbon atoms of the hydrocarbon chain is replaced independently with an —O—, —S or —NR— group and wherein 1, 2, 3, 4, 5 or 6 of the carbon atoms of the hydrocarbon chain is substituted independently with an oxo or thioxo group, and wherein each R is independently an H, saturated ($C_1$-$C_{10}$) hydrocarbon or unsaturated ($C_2$-$C_{10}$) hydrocarbon chain and wherein $A^2$ is connected to B by an ester, amide, thioester or thioamide group.

In one embodiment A is

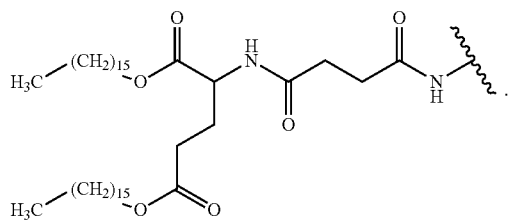

In one embodiment

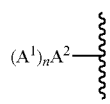

is

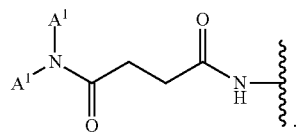

In one embodiment:
(a) B is a spacer group or
(b) B is absent provided that when B is absent, the polynucleotide comprises one or more guanine nucleotides and is greater than 25 nucleotides in length.

In one embodiment:
(a) B is a spacer group or
(b) B is absent provided that when B is absent, the polynucleotide comprises one or more guanine nucleotides and is greater than 10 nucleotides in length.

In one embodiment B is a spacer group.

In one embodiment B is a saturated or unsaturated ($C_{10}$-$C_{16}$) hydrocarbon chain wherein 1 or 2 of the carbon atoms of the hydrocarbon chain is replaced independently with an —O—, —S or —NR— group and wherein 1 or 2 of the carbon atoms of the hydrocarbon chain is optionally substituted independently with an oxo or thioxo group, and wherein each R is independently H, saturated ($C_1$-$C_{10}$) hydrocarbon chain or unsaturated ($C_2$-$C_{10}$) hydrocarbon chain.

In one embodiment B is a saturated or unsaturated ($C_{10}$-$C_{16}$) hydrocarbon chain wherein 1 or 2 of the carbon atoms of the hydrocarbon chain is replaced independently with an —O—, —S or —NR— group and wherein 1 or 2 of the carbon atoms of the hydrocarbon chain is optionally substituted independently with an oxo or thioxo group, and wherein each R is independently H, saturated ($C_1$-$C_{10}$) hydrocarbon chain or unsaturated ($C_2$-$C_{10}$) hydrocarbon. chain In one embodiment B is a saturated or unsaturated ($C_{10}$-$C_{16}$) hydrocarbon chain wherein 1 or 2 of the carbon atoms of the hydrocarbon chain are replaced independently with an —O—, —S or —NR— group and wherein 1 or 2 of the carbon atoms of the hydrocarbon chain are substituted independently with an oxo or thioxo group, and wherein each R is independently H, saturated ($C_1$-$C_{10}$) hydrocarbon chain or unsaturated ($C_2$-$C_{10}$) hydrocarbon chain.

In one embodiment B is a saturated or unsaturated ($C_{10}$-$C_{16}$) hydrocarbon chain wherein 1 or 2 of the carbon atoms of the hydrocarbon chain is optionally replaced independently with an —O—, —S or —NR— group and wherein 1 or 2 of the carbon atoms of the hydrocarbon chain is substituted independently with an oxo or thioxo group, and wherein each R is independently H, saturated ($C_1$-$C_{10}$) hydrocarbon chain or unsaturated ($C_2$-$C_{10}$) hydrocarbon chain.

In one embodiment B is a saturated or unsaturated ($C_{10}$-$C_{16}$) hydrocarbon chain wherein 1 or 2 of the carbon atoms of the hydrocarbon chain is optionally replaced independently with an —O—, —S or —NR— group and wherein 1 or 2 of the carbon atoms of the hydrocarbon chain is substituted independently with an oxo or thioxo group, and wherein each R is independently H, saturated ($C_1$-$C_{10}$) hydrocarbon chain or unsaturated ($C_2$-$C_{10}$) hydrocarbon. chain In one embodiment B is a saturated or unsaturated ($C_{10}$-$C_{16}$) hydrocarbon chain wherein 1 or 2 of the carbon atoms of the hydrocarbon chain are optionally replaced independently with an —O—, —S or —NR— group and wherein 1 or 2 of the carbon atoms of the hydrocarbon chain are substituted independently with an oxo or thioxo group, and wherein each R is independently H, saturated ($C_1$-$C_{10}$) hydrocarbon chain or unsaturated ($C_2$-$C_{10}$) hydrocarbon chain.

In one embodiment B is

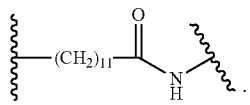

In one embodiment B is

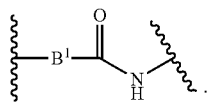

wherein $B^1$ is saturated or unsaturated ($C_5$-$C_{20}$) hydrocarbon chain.

In one embodiment B is not a polyethylene glycol (PEG).

In one embodiment C is absent.

In one embodiment C is a saturated or unsaturated ($C_2$-$C_{10}$) hydrocarbon chain.

In one embodiment C is a saturated or unsaturated ($C_4$-$C_8$) hydrocarbon chain.

In one embodiment C is a saturated ($C_4$-$C_8$) hydrocarbon chain.

In one embodiment C is hexyl.

In one embodiment C is a saturated or unsaturated ($C_2$-$C_{10}$) hydrocarbon chain, wherein one or more of the carbon atoms of the hydrocarbon chain is optionally replaced independently with an —O—, —S or —NR— group and wherein one or more of the carbon atoms of the hydrocarbon chain is optionally substituted independently with an oxo, thioxo or hydoxyl group, and wherein each R is independently H, saturated ($C_1$-$C_{10}$) hydrocarbon chain or unsaturated ($C_2$-$C_{10}$) hydrocarbon chain.

In one embodiment C is a saturated or unsaturated ($C_4$-$C_8$) hydrocarbon chain wherein one or more of the carbon atoms of the hydrocarbon chain is optionally replaced independently with an —O—, —S or —NR— group and wherein one or more of the carbon atoms of the hydrocarbon chain is optionally substituted independently with an oxo, thioxo or hydoxyl group, and wherein each R is independently H, saturated ($C_1$-$C_{10}$) hydrocarbon chain or unsaturated ($C_2$-$C_{10}$) hydrocarbon chain.

In one embodiment C is a saturated ($C_4$-$C_8$) hydrocarbon chain wherein one or more of the carbon atoms of the hydrocarbon chain is optionally replaced independently with an —O—, —S or —NR— group and wherein one or more of the carbon atoms of the hydrocarbon chain is optionally substituted independently with an oxo, thioxo or hydoxyl group, and wherein each R is independently H, saturated ($C_1$-$C_{10}$) hydrocarbon chain or unsaturated ($C_2$-$C_{10}$) hydrocarbon chain.

In one embodiment C is:

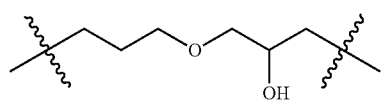 [SMILES: *CCCOCC(O)C*]

In one embodiment D is single stranded DNA

In one embodiment D is single stranded RNA

In one embodiment D is single stranded DNA comprising 5-50 nucleotides.

In one embodiment D is single stranded RNA comprising 5-50 nucleotides.

In one embodiment D is any of the polynucleotides of FIG. 1.

In one embodiment D is single stranded DNA does not include any guanine nucleotides.

In one embodiment D is an aptamer.

In one embodiment D is connected to the C or B of formula I at the 5' end of the polynucleotide.

In one embodiment D is connected to the C or B of formula I at the 3' end of the polynucleotide.

In one embodiment D is not a polynucleotide which has fractalkine binding activity In one embodiment D is not the nucleotide sequence

```
                                          (SEQ ID NO: 2)
GGGGTGGGTGGGGGGCACGTGTGGGGGCGGCCAGGGTGCT.
```

In one embodiment D is the nucleotide sequence

```
                                          (SEQ ID NO: 2)
GGGGTGGGTGGGGGGCACGTGTGGGGGCGGCCAGGGTGCT
```

In one embodiment D is not the nucleotide sequence

```
                                          (SEQ ID NO: 2)
GGGGTGGGTGGGGGGCACGTGTGGGGGCGGCCAGGGTGCT
``` or a sequence having at least 80% identity to said sequence.

In one embodiment D is the nucleotide sequence

```
                                          (SEQ ID NO: 2)
GGGGTGGGTGGGGGGCACGTGTGGGGGCGGCCAGGGTGCT
``` or a sequence having at least 80% identity to said sequence.

In one embodiment D is the nucleotide sequence

```
                                          (SEQ ID NO: 3)
                    GGGGGTTCTC
``` or a sequence having at least 80% identity to said sequence.

In one embodiment D is not the nucleotide sequence

```
                                          (SEQ ID NO: 2)
5'-GGGGTGGGTGGGGGGCACGTGTGGGGGCGGCCAGGGTGCT-3'.
```

In one embodiment D is the nucleotide sequence

```
                                          (SEQ ID NO: 2)
5'-GGGGTGGGTGGGGGGCACGTGTGGGGGCGGCCAGGGTGCT-3'.
```

In one embodiment D is not the nucleotide sequence

```
                                          (SEQ ID NO: 2)
5'-GGGGTGGGTGGGGGGCACGTGTGGGGGCGGCCAGGGTGCT-3'
``` or a sequence having at least 80% identity to said sequence.

In one embodiment D is the nucleotide sequence (SEQ ID NO: 2)
5'-GGGGTGGGTGGGGGCACGTGTGGGGGCGGCCAGGGTGCT-3' or a sequence having at least 80% identity to said sequence.
In one embodiment D is the nucleotide sequence (SEQ ID NO: 3)
5'-GGGGGTTCTC-3' or a sequence having at least 80% identity to said sequence.

In one embodiment A is a saturated or unsaturated ($C_{20}$-$C_{80}$) hydrocarbon chain wherein one or more of the carbon atoms of the hydrocarbon chain is replaced independently with an —O—, —S—, N or —NR— group and wherein one or more of the carbon atoms of the hydrocarbon chain is optionally substituted independently with an oxo or thioxo group, and wherein each R is independently an H, saturated ($C_1$-$C_{10}$) hydrocarbon chain or unsaturated ($C_2$-$C_{10}$) hydrocarbon chain.

In one embodiment A is a saturated or unsaturated ($C_{20}$-$C_{70}$) hydrocarbon chain wherein one or more of the carbon atoms of the hydrocarbon chain is independently replaced with an —O—, —S—, N or —NR— group and wherein one or more of the carbon atoms of the hydrocarbon chain is optionally substituted independently with an oxo or thioxo group, and wherein each R is independently H, saturated ($C_1$-$C_{10}$) hydrocarbon or unsaturated ($C_2$-$C_{10}$) hydrocarbon chain.

In one embodiment A is a saturated or unsaturated ($C_{30}$-$C_{70}$) hydrocarbon chain wherein one or more of the carbon atoms of the hydrocarbon chain is replaced independently with an —O—, —S—, N or —NR— group and wherein one or more of the carbon atoms of the hydrocarbon chain is optionally substituted independently with an oxo or thioxo group, and wherein each R is independently H, saturated ($C_1$-$C_{10}$) hydrocarbon chain or unsaturated ($C_2$-$C_{10}$) hydrocarbon chain.

In one embodiment 1, 2, 3, 4, 5, 6, 7 or 8 of the carbon atoms of the hydrocarbon chain of A are replaced independently with an —O—, —S—, N or —NR— group and wherein 1, 2, 3, 4, 5, 6, 7 or 8 of the carbon atoms of the hydrocarbon chain of A is substituted independently with an oxo or thioxo group, and wherein each R is independently an H, saturated ($C_1$-$C_{10}$) hydrocarbon chain or unsaturated ($C_2$-$C_{10}$) hydrocarbon chain.

In one embodiment 1, 2, 3, 4, 5 or 6 of the carbon atoms of the hydrocarbon chain of A are replaced independently with an —O—, —S—, N or —NR— group and wherein 1, 2, 3, 4, 5 or 6 of the carbon atoms of the hydrocarbon chain of A substituted with an oxo or thioxo group, and wherein each R is independently an H, saturated ($C_1$-$C_{10}$) hydrocarbon chain or unsaturated ($C_2$-$C_{10}$) hydrocarbon chain.

In one embodiment A has the formula:

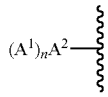

wherein:
each $A^1$ is independently a saturated or unsaturated ($C_5$-$C_{30}$) hydrocarbon chain;

$A^2$ is a saturated or unsaturated ($C_5$-$C_{25}$) hydrocarbon chain wherein one or more of the carbon atoms of the hydrocarbon chain is replaced independently with an —O—, —S—, N or —NR— group and wherein one or more of the carbon atoms of the hydrocarbon chain is optionally substituted independently with an oxo or thioxo group, and wherein each R is independently an H, saturated ($C_1$-$C_{10}$) hydrocarbon chain or unsaturated ($C_2$-$C_{10}$) hydrocarbon chain; and n is 1, 2, 3 or 4.

In one embodiment $A^2$ is a saturated or unsaturated ($C_4$-$C_{20}$) hydrocarbon chain wherein one or more of the carbon atoms of the hydrocarbon chain is replaced independently with an O, S, N or NR group and wherein one or more of the carbon atoms of the hydrocarbon chain is optionally substituted independently with an oxo or thioxo group, and wherein each R is independently an H, saturated ($C_1$-$C_{10}$) hydrocarbon chain or unsaturated ($C_2$-$C_{10}$) hydrocarbon chain.

In one embodiment $A^2$ is a saturated ($C_{10}$-$C_{20}$) hydrocarbon chain wherein 1, 2, 3, 4, 5, 6, 7 or 8 of the carbon atoms of the hydrocarbon chain is replaced independently with an —O—, —S—, N or —NR— group and wherein 1, 2, 3, 4, 5, 6, 7 or 8 of the carbon atoms of the hydrocarbon chain is substituted independently with an oxo or thioxo group, and wherein each R is independently an H, saturated ($C_1$-$C_{10}$) hydrocarbon chain or unsaturated ($C_2$-$C_{10}$) hydrocarbon chain.

In one embodiment $A^2$ is a saturated ($C_{10}$-$C_{16}$) hydrocarbon chain wherein 1, 2, 3, 4, 5 or 6 of the carbon atoms of the hydrocarbon is replaced independently with an —O—, —S—, N or —NR— group and wherein 1, 2, 3, 4, 5 or 6 of the carbon atoms of the hydrocarbon chain is substituted with an oxo or thioxo group, and wherein each R is independently an H, saturated ($C_1$-$C_{10}$) hydrocarbon chain or unsaturated ($C_2$-$C_{10}$) hydrocarbon chain.

In one embodiment $A^2$ is a saturated ($C_{10}$-$C_{16}$) hydrocarbon chain wherein 1, 2, 3, 4, 5 or 6 of the carbon atoms of the hydrocarbon chain is replaced independently with an —O—, —S—, N or —NR— group and wherein 1, 2, 3, 4, 5 or 6 of the carbon atoms of the hydrocarbon chain is substituted independently with an oxo or thioxo group, and wherein each R is independently an H, saturated ($C_1$-$C_{10}$) hydrocarbon chain or unsaturated ($C_2$-$C_{10}$) hydrocarbon chain and wherein $A^2$ is connected to B by an ester, amide, thioester or thioamide group.

In one embodiment A is

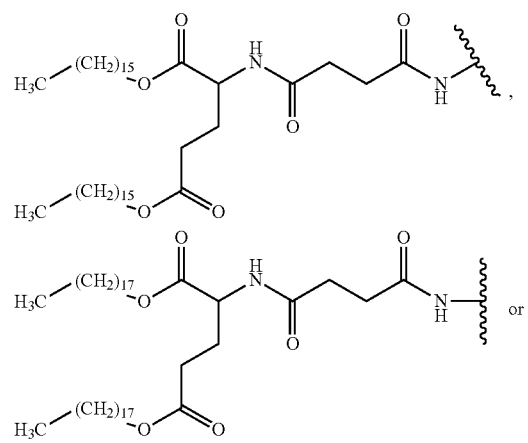

-continued

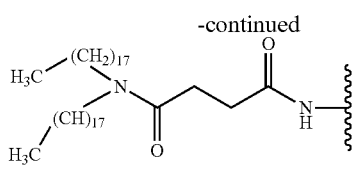

In cases where nucleic acid amphiphiles are sufficiently basic or acidic, a salt of the nucleic acid amphiphiles or nanostructure can be useful as an intermediate for isolating or purifying the amphiphile or nanostructure. Additionally, administration of a nanostructure such as a nanotube comprising a nucleic acid amphiphile as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The nanostructures (e.g., nanotubes) described herein can be used to deliver therapeutic agents to mammals and/or the nanostructures (e.g., nanotubes) can be made to target specific biological targets in a mammal. Accordingly, it may be desirable to formulate the nanostructures (e.g., nanotubes) as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the nanostructures (e.g., nanotubes) may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. If the nanotube is being used to deliver a therapeutic agent (e.g., active agent) the amount of the active agent and nanotube may be varied. The amount of active agent in such therapeutically useful compositions is such that an effective dosage level will be obtained. The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The nanostructures (e.g., nanotubes) may also be administered intravenously or intraperitoneally by infusion or injection. Solutions of the nanotube or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Useful dosages of the nanostructures (e.g., nanotubes) and/or therapeutic agents being delivered by the nanostructures (e.g., nanotubes) can be determined by comparing their in vitro activity, and in vivo activity in animal models. Methods for the extrapolation of effective dosages in mice, and other animals, to humans are known to the art; for example, see U.S. Pat. No. 4,938,949.

success of the synthesis the molecular weights of the purified amphiphiles were identified by liquid chromatography-mass spectroscopy (LC-MS) (Zorbax $C_3$ 300 Å SB column, 50-80% B over 15 min, buffer A: $H_2O$+15 mM ammonium acetate, buffer B: acetonitrile). Mass spectroscopy data were acquired with an Agilent MSD ion trap (FIG. 7). The structures of prepared compounds are shown in FIG. 1 and Schemes 1 and 2.

Scheme 1 (compounds 1A-1H with spacer)

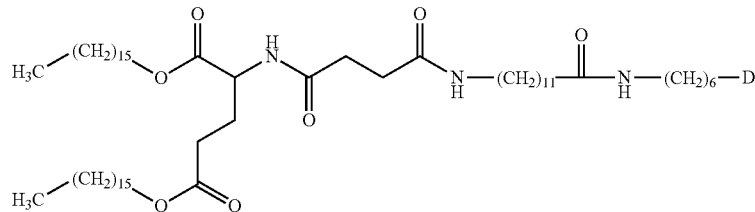

The amount of the nanostructures (e.g., nanotubes) and/or therapeutic agents being delivered by the nanotube, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations The invention will now be illustrated by the following non-limiting Example.

EXAMPLE 1

Materials and methods
Materials

Toluene, chloroform, acetone, methanol, and triethylamine were purchased from Fischer Chemical (Hanover Park, Ill.). ssDNA was purchased from Integrated DNA Technologies (Coralville, Iowa), cetyl trimethylammonium bromide from Acros Organics (Morris Plains, N.J.), and hexafluroisopropanol (HFIP) from Oakwood Products Inc (West Columbia, S.C.). All other chemicals were purchased from Sigma-Aldrich (St Louis, Mo.). Lacey Formvar/carbon, 200 mesh, copper grids were purchased from Ted Pella Inc. (Redding, Calif.) and 1.0 mm path-length quartz capillaries from Charles Supper Company (Natick, Mass.).

ssDNA-amphiphile synthesis

The ssDNA sequences with an amino-$C_6$ linker attached to their 5' end were conjugated to the N-hydroxysuccinimide (NHS) activated $(C_{16})_2$-Glu-$C_2$ tail (A. Mardilovich et al., Biomacromolecules, 2004, 5, 950-957) (NoSPR), or to the tails via a $C_{12}$ spacer using a solution-phase synthesis as described previously (T. R. Pearce, et al., Chem. Commun., 2014, 50, 210-212) to create ssDNA-amphiphiles. Unreacted ssDNA was separated from the ssDNA-amphiphile using reverse-phase high performance liquid chromatography (HPLC). HPLC information: Zorbax $C_8$ 300 Å SB column, 5-90% B over 25 min, buffer A: $H_2O$+10% methanol, 100 mM HFIP, 14.4 mM triethylamine (TEA), buffer B: methanol, 100 mM HFIP, 14.4 mM TEA. To confirm the Compound number: value for D

1A: D =
(SEQ ID NO: 4)
5'-TTCTATTCTC-3'

1B: D =
(SEQ ID NO: 5)
5'-CCAATTAATT-3'

1C: D =
(SEQ ID NO: 6)
5'-TTCTATTCTCACATTTCATCTATTA-3'

1D: D =
(SEQ ID NO: 7)
5'-TTCTATTCTCACATTTCATCTATTAAACCACCAATTAATT-3'

1E: D =
(SEQ ID NO: 3)
5'-GGGGGTTCTC-3'

1F: D =
(SEQ ID NO: 8)
5'-GGGGGTAATT-3'

1G: D =
(SEQ ID NO: 9)
5'-GGGGGTTCTCACATTTCATCTATTA-3'

1H: D =
(SEQ ID NO: 10)
5'-GGGGGTTCTCACATTTCATCTATTAAACCACCAATTAATT-3'

Scheme 2 (compounds 1J-1T without spacer)

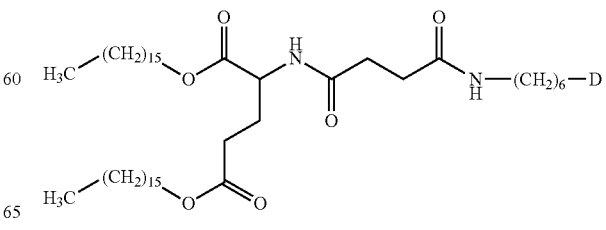

Compound: value for D

1J: D =
5'-TTCTATTCTC-3' (SEQ ID NO: 4)

1K: D =
5'-CCAATTAATT-3' (SEQ ID NO: 5)

1L: D =
5'-TTCTATTCTCACATTTCATCTATTA-3' (SEQ ID NO: 6)

1M: D =
5'-TTCTATTCTCACATTTCATCTATTAAACCACCAATTAATT-3' (SEQ ID NO: 7)

1N: D =
5'-GGGGGTTCTC-3' (SEQ ID NO: 3)

1O: D =
5'-GGGGGTAATT-3' (SEQ ID NO: 8)

1P: D =
5'-GGGGGTTCTCACATTTCATCTATTA-3' (SEQ ID NO: 9)

1Q: D =
5'-GGGGGTTCTCACATTTCATCTATTAAACCACCAATTAATT-3' (SEQ ID NO: 10)

1S: D =
5'-GGGTGGGTGGGTATTTCATCTATTA-3' (SEQ ID NO: 11)

1T: D =
5'-GGGTGGGTGGGTATTTCATCTATTAAACCACCAATTAATT-3' (SEQ ID NO: 12)

Scheme 3A shows the chemical steps used to prepare compounds described herein.

Scheme 3A

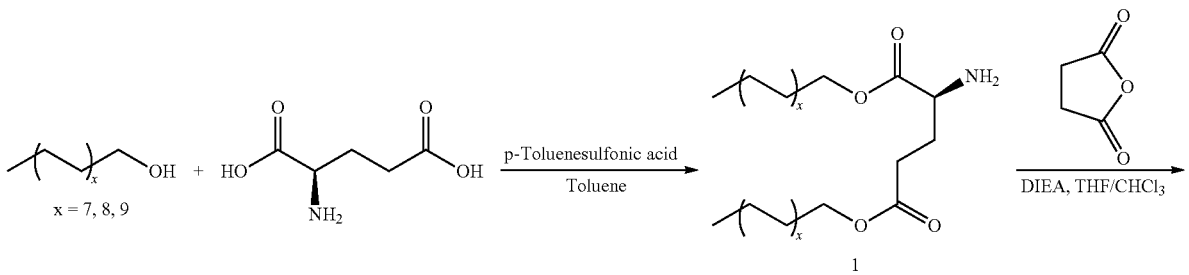

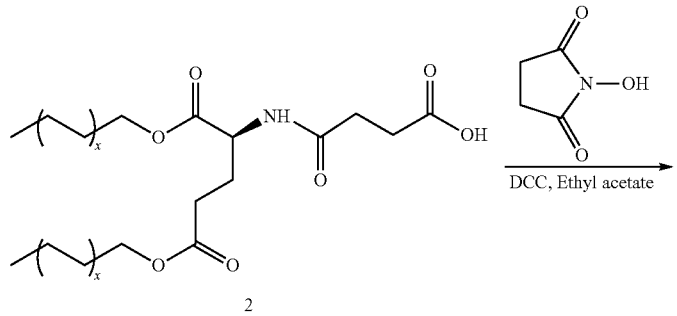

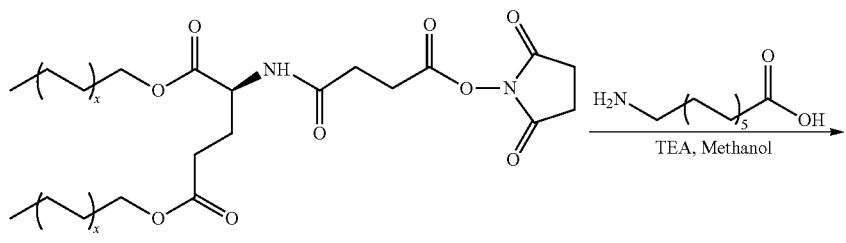

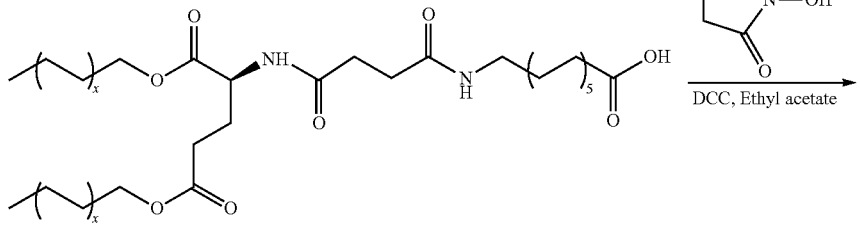

4

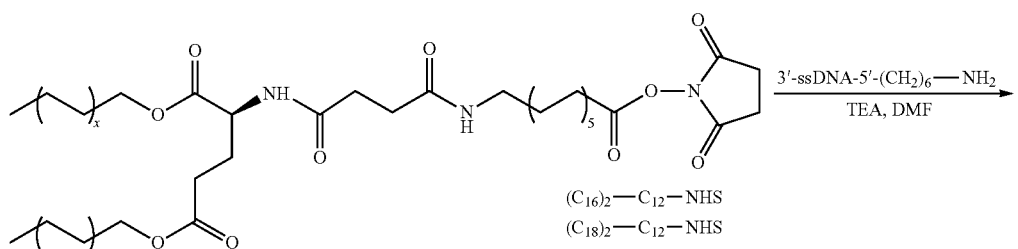

(C$_{16}$)$_2$—C$_{12}$—NHS
(C$_{18}$)$_2$—C$_{12}$—NHS
(C$_{20}$)$_2$—C$_{12}$—NHS

5

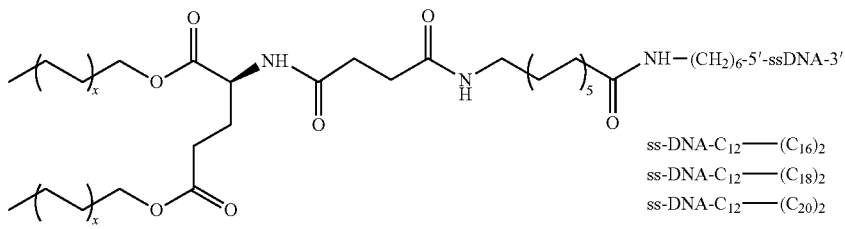

ss-DNA-C$_{12}$——(C$_{16}$)$_2$
ss-DNA-C$_{12}$——(C$_{18}$)$_2$
ss-DNA-C$_{12}$——(C$_{20}$)$_2$

6

Glutamic acid and p-toluenesulfonate (1.2× molar excess) were first mixed in toluene and refluxed for 1 h at 130° C. Then alcohol (hexadecanol, octadecanol or eicosanol) (2.2× molar excess) was added. The mixture was heated until an equimolar amount of water was recovered in a Dean-Stark trap. The toluene was removed and the product 1 recrystallized from acetone three times. Then 1 was dissolved in CHCl$_3$/THF (50/50%, v/v) at 50° C. and 15% molar excess of succinic anhydride and 50% molar excess of N,N-diisopropylethylamine (DIEA) were added. After 6 h, the solvents were evaporated and the product 2 was recrystallized from ethyl acetate. Then N-hydroxysuccinimide (NHS, 1.5× molar excess) was added to a solution of 2 in dichloromethane (DCM) at room temperature. After cooling to 0° C., N,N'-dicyclohexylcarbodiimide (DCC, 2× molar excess) was added. The solution was stirred for 1 h at 0° C. and then overnight at room temperature. The precipitated dicyclohexyl urea (DCU) was filtered off, and solvent was removed in vacuum. The product 3 was recrystallized from ethyl acetate. The NHS-activated 3 was then reacted with excess spacer, for example C$_{12}$, (1.5× molar excess) in methanol for 6 h at 50° C. Then methanol was removed and DCM was added to dissolve the product 4. The excess spacer (didn't dissolve in DCM) was removed by filtration. DCM was then evaporated and the product 4 was recrystallized from ethyl acetate. As a last step, 4 was activated by NHS to obtain the product 5.

To link the activated tails with the ssDNA, 1.5× molar excess cetyl trimethylammonium bromide (CTAB) dissolved in water was added to the ssDNA. The ammonium (NH$_4^+$) moiety of CTAB is electrostatically attracted to the PO$_4^-$ of the ssDNA backbone, which renders the ssDNA soluble in dimethylformamide (DMF). A 10× molar excess of activated tails 5 and trace triethylamine (TEA) were added to the CTAB-ssDNA complexes dissolved in DMF and the reaction was stirred at 50° C. for 24 h. After 24 h, the DMF was removed by evaporation and the ssDNA-amphiphiles and any unreacted ssDNA were purified by ethanol precipitation to remove unreacted tails and CTAB. Finally ssDNA-amphiphile 6 was purified by reverse-phase high performance liquid chromatography (RP-HPLC).

Scheme 3B shows the chemical steps used to prepare compounds described herein.

Scheme 3B

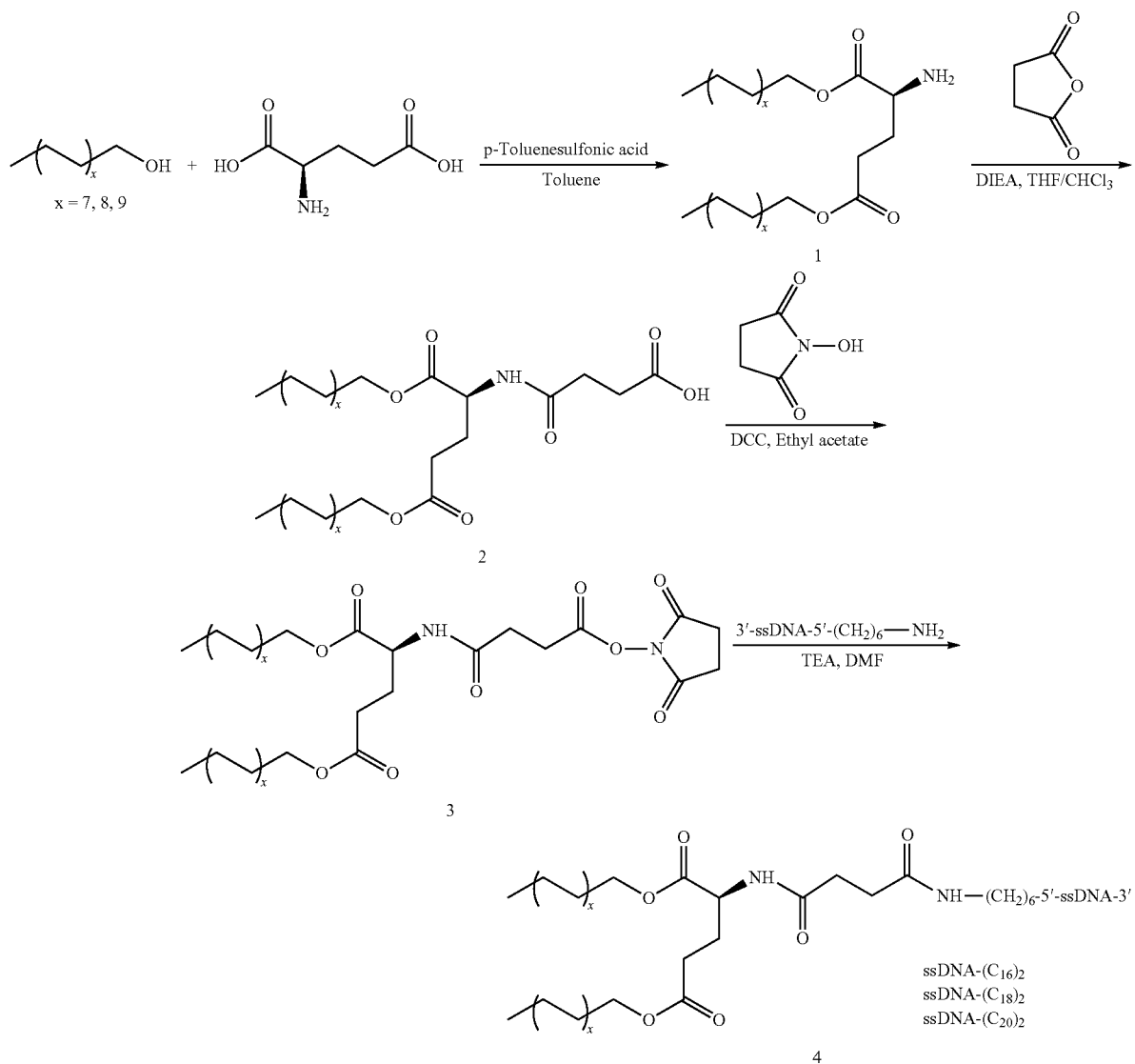

Glutamic acid and p-toluenesulfonate (1.2× molar excess) were first mixed in toluene and refluxed for 1 h at 130° C. Then alcohol (hexadecanol, octadecanol or eicosanol) (2.2× molar excess) was added. The mixture was heated until an equimolar amount of water was recovered in a Dean-Stark trap. The toluene was removed and the product 1 recrystallized from acetone three times. Then 1 was dissolved in $CHCl_3$/THF (50/50%, v/v) at 50° C. and 15% molar excess of succinic anhydride and 50% molar excess of N,N-diisopropylethylamine (DIEA) were added. After 6 h, the solvents were evaporated and the product 2 was recrystallized from ethyl acetate. Then N-hydroxysuccinimide (NHS, 1.5× molar excess) was added to a solution of 2 in dichloromethane (DCM) at room temperature. After cooling to 0° C., N,N'-dicyclohexylcarbodiimide (DCC, 2× molar excess) was added. The solution was stirred for 1 h at 0° C. and then overnight at room temperature. The precipitated dicyclohexyl urea (DCU) was filtered off, and solvent was removed in vacuum. The product 3 was recrystallized from ethyl acetate.

To link the activated tails with the ssDNA, 1.5× molar excess cetyl trimethylammonium bromide (CTAB) dissolved in water was added to the ssDNA. The ammonium ($NH_4^+$) moiety of CTAB is electrostatically attracted to the $PO_4^-$ of the ssDNA backbone, which renders the ssDNA soluble in dimethylformamide (DMF). A 10× molar excess of activated tails 3 and trace triethylamine (TEA) were added to the CTAB-ssDNA complexes dissolved in DMF and the reaction was stirred at 50° C. for 24 h. After 24 h, the DMF was removed by evaporation and the ssDNA-amphiphiles and any unreacted ssDNA were purified by ethanol precipitation to remove unreacted tails and CTAB. Finally ssDNA-amphiphile 4 was purified by reverse-phase high performance liquid chromatography (RP-HPLC).

Cryogenic transmission electron microscopy (cryo-TEM)

4.5 µL of 500 µM amphiphile solutions were deposited onto lacey Formvar/carbon copper grids that had been treated with glow discharge for 60 sec and vitrified in liquid ethane by Vitrobot (Vitrobot parameters: 4 sec blot time, 0 offset, 3 sec wait time, 3 sec relax time, ambient humidity).

The grids were kept under liquid nitrogen until they were transferred to a Tecnai G2 Spirit TWIN 20-120 kV/LaB6 TEM operated with an acceleration voltage of 120 keV. Images were captured using an Eagle 2 k CCD camera.

Circular dichroism (CD)

500 µM solutions of ssDNA-amphiphiles were diluted to 20 µM with Milli-Q water and transferred to a 0.1 cm path length cuvette. CD spectra from 320-200 nm were collected using a Jasco J-815 spectrapolarimeter using a read speed of 50 nm/min in 1 nm steps. 3 accumulations per amphiphile solution were recorded with the background spectrum from the water automatically subtracted. The accumulations were averaged and the raw ellipticity values were converted to molar ellipticity.

Results ssDNA-amphiphile synthesis

An initial ssDNA headgroup 40 nucleotides in length was created using only adenine (A), cytosine (C), and thymine (T) nucleobases selected at random. This guanine-free (NoG) 40 nucleotide headgroup was then used to create headgroups with 10 and 25 nucleotides that conserved the nucleotide order at the 5' end of the headgroup (FIG. 1A). A second version of the 10 nucleotide sequence was created that conserved the 3' end of the headgroup, which provided a headgroup with the same length but a different random nucleotide sequence. Nucleotides containing the guanine nucleobase were used to replace some nucleotides at the 5' ends of headgroups, either as a single string of five guanines ($G_5$) or as a repeat of $(GGGT)_3$ (FIG. 1A) to produce headgroups that had potential to form intermolecular G-quadruplex interactions. The 5' ends of the ssDNA headgroups were conjugated to dialkyl tails via $C_{12}$ spacer molecules or directly to the tails without the use of a spacer (FIG. 1B). Successful conjugation was confirmed by LC-MS (FIG. 7).

Figure 2:
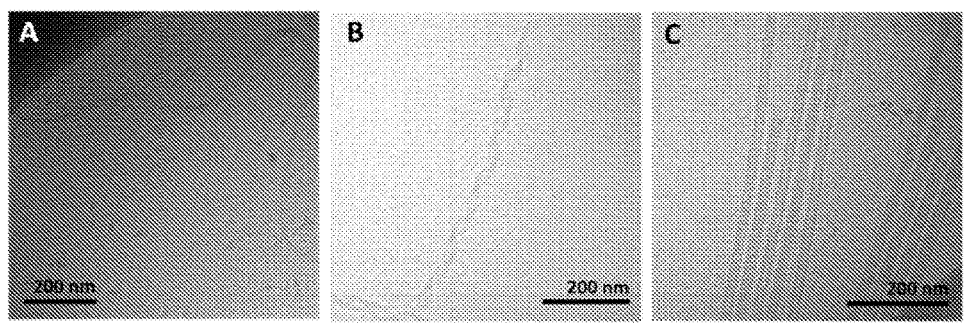
FIGS. 2A-2C show cryo-TEM images of ssDNA-amphiphiles forming 2A) a twisted nanotape, 2B) helical nanotapes and 2C) nanotubes. All amphiphiles contained the $C_{12}$ spacer and either the A) 25 nt NoG, B) 10 nt-2 NoG, or C) 10 nt-1 NoG headgroups.

Self-assembly of ssDNA-amphiphiles with NoG headgroups and with or without a $C_{12}$ spacer Amphiphiles with NoG headgroups attached to the hydrophobic tails via $C_{12}$ spacers were dissolved in Milli-Q water to form 500 µM solutions and were immediately (<30 min) deposited onto cryo-TEM grids, vitrified in liquid ethane, and imaged to visualize the morphology of the self-assembled structures formed by the amphiphiles. A variety of structures were present in each of the amphiphile solutions with either a 10, 25 or 40 nucleotide NoG headgroup: globular micelles, twisted nanotapes, helical nanotapes, and nanotubes (FIG. 2). Of particular interest were the nanotube structures, which have never before been formed via self-assembly of ssDNA-amphiphiles. Analysis of an image of a nanotube created from amphiphiles with a 25 nucleotide NoG headgroup and a $C_{12}$ spacer obtained at 0° and 45° stage-tilt (FIG. 8A) showed that the diameter of the nanotube was unchanged when viewed from different angles, demonstrating the cylindrical shape of the nanotube. Line-scan analysis of the nanotube structure (FIG. 8B) revealed a pattern of contrast consistent with that of a hollow tube, confirming the cylindrical structures are nanotubes with 34 nm diameter and walls approximately 10 nm thick.

The cylindrical nanotube structures observed in the samples with headgroups containing 10 nucleotides had an overall average diameter of 30±4 nm, while samples with the 25 and 40 nucleotide headgroups produced structures with average diameters of 32±3 nm and 31±1 nm, respectively. While the overall average diameters of the nanotubes produced by amphiphiles of different headgroup lengths were similar, the diameters of the nanotubes vary between different nanotubes in the same sample, and in some cases there was also variation along the length of a single nanotube. The lengths of the nanotubes formed by amphiphiles containing the 10, 25, and 40 nucleotide headgroups were variable, with each sample producing nanotubes 100s to 1,000s of nm in length and no apparent difference in the typical length between amphiphiles with different headgroups.

Twisted and helical nanotapes were also observed in all the samples, but in lower numbers than the nanotubes. The majority of the twisted nanotapes in each of the different amphiphile samples did not twist in a periodic manner and had widths ranging from 20 to 50 nm. However, in a few instances the twisted nanotapes were observed to twist in a periodic manner with an average pitch length of 132±6 nm and an average width of 24±2 nm. The helical nanotapes observed in each of the different amphiphile samples displayed clear periodicity with an average pitch length of 129±7 nm, similar to that observed in the twisted nanotape structures. However, the average width of the helical nanotapes was 38±4 nm, substantially larger than that of the regularly twisted nanotapes. Also present in all of the samples were globular micelles, some of which were spherical and some were weakly ellipsoidal. Micelles formed by each of the amphiphile samples had diameters (or ellipsoid axes lengths) of 9-20 nm with no measurable difference in average size between the amphiphiles with different length headgroups.

The same NoG headgroups were also conjugated directly to hydrophobic tails without the use of the $C_{12}$ spacer and imaged with cryo-TEM. These amphiphiles also formed micelles but were not observed to form any of the larger, more complex, bilayer nanotape and nanotube structures (Table 1). The inability for amphiphiles with NoG headgroups and lacking the $C_{12}$ spacer to form more complex bilayer structures was not surprising as it has been previously shown that amphiphiles with headgroups of similar lengths that lack G-quadruplex interactions only assemble into globular micelles T. R. Pearce, et al., *Chem. Commun.*, 2014, 50, 210-212; B. Waybrant, et al., *Langmuir*, 2014, DOI: 10.1021/la500403v; H. Liu, et al., *Chem. Eur. J.*, 2010, 16, 3791-3797).

Figure 9:
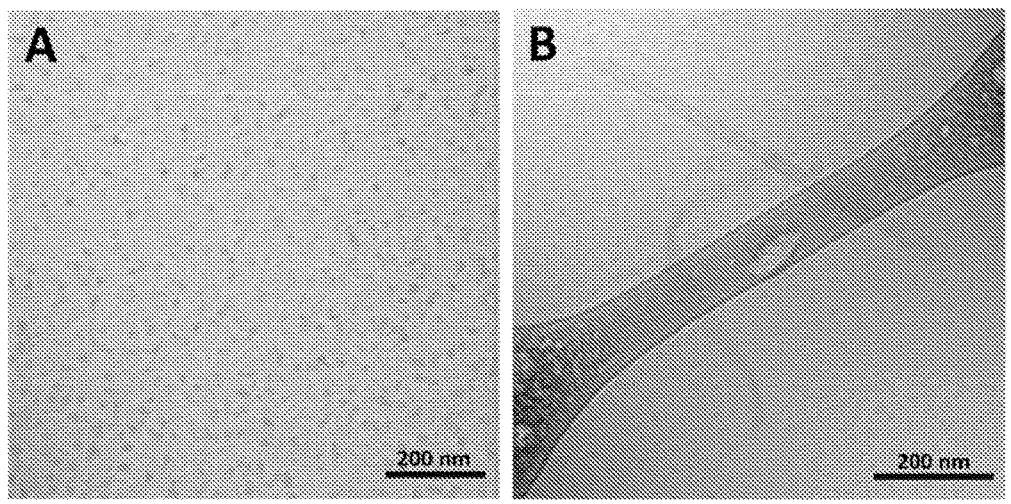
FIGS. 9A-9B shows the cryo-TEM images of 9A) micelles formed by ssDNA-amphiphiles with a 10 nucleotide (10 nt-1) $G_5$-modified headgroup lacking the $C_{12}$ spacer, and 9B) a twisted nanotape and nanotube formed by amphiphiles with a 40 nucleotide $G_5$-modified headgroup, without the $C_{12}$ spacer.

Self-assembly of ssDNA-amphiphiles with guanine-modified headgroups and without a $C_{12}$ spacer To test if the presence of guanines positioned immediately adjacent to the site of conjugation to the hydrophobic tail could produce nanotape and nanotube structures in the absence of the $C_{12}$ spacer a third set of amphiphiles was created that included the $G_5$ modification in the 10, 25, and 40 nucleotide ssDNA headgroups, with the headgroups directly linked to the hydrophobic tails (as shown in FIG. 1). This was to test whether the inclusion of the five guanines would produce intermolecular parallel G-quadruplex interactions between the headgroups that would bring the headgroups together and minimize the headgroup area in a similar manner as the $C_{12}$ spacer, thus allowing the nanotapes to form. These amphiphile samples were dissolved in Milli-Q water at 500 µM, vitrified and imaged with cryo-TEM to determine their self-assembly behaviour. The only structures observed in the amphiphile samples with 10 and 25 nucleotide headgroups were spherical and weakly ellipsoidal micelles that were of similar sizes as observed in the amphiphile samples with the NoG headgroups. Micelles of similar shape and size were also the most prevalent structure observed in the amphiphile samples with the 40 nucleotide $G_5$ headgroup, but twisted and helical nanotapes and nanotubes that were similar to those produced by the NoG headgroups with the $C_{12}$ spacer were also observed infrequently (Table 1, FIG. 9).

TABLE 1

A summary of the structures observed with cryo-TEM in each of the ssDNA-amphiphile samples shown in FIG. 1.

| Sample | Twisted nanotape | Helical nanotape | Nanotube |
|---|---|---|---|
| Compound 1A, 1B (10 nt NoG $C_{12}$) | Yes | Yes | Yes |
| Compound 1C (25 nt NoG $C_{12}$) | Yes | Yes | Yes |
| Compound 1D (40 nt NoG $C_{12}$) | Yes | Yes | Yes |
| Compound 1E, 1F (10 nt $G_5$ $C_{12}$) | Yes | Yes | Yes[a] |
| Compound 1G (25 nt $G_5$ $C_{12}$) | Yes | Yes | Yes |
| Compound 1H (40 nt $G_5$ $C_{12}$) | Yes | Yes | Yes |
| Compound 1J, 1K (10 nt NoG NoSPR) | No | No | No |
| Compound 1L (25 nt NoG NoSPR) | No | No | No |
| Compound 1M (40 nt NoG NoSPR) | No | No | No |
| Compound 1N, 1O (10 nt $G_5$ NoSPR) | No | No | No |
| Compound 1P (25 nt $G_5$ NoSPR) | No | No | No |
| Compound 1Q (40 nt $G_5$ NoSPR) | Yes[b] | Yes[b] | Yes[b] |
| Compound 1S (25 nt $(GGGT)_3$ (SEQ ID NO: 1) NoSPR) | Yes[b] | No | No |
| Compound 1T (40 nt $(GGGT)_3$ (SEQ ID NO: 1) NoSPR) | Yes[b] | No | No |

[a]Nanotubes were substantially shorter in this sample than in all others.
[b]Structures were observed infrequently.

Figure 10:
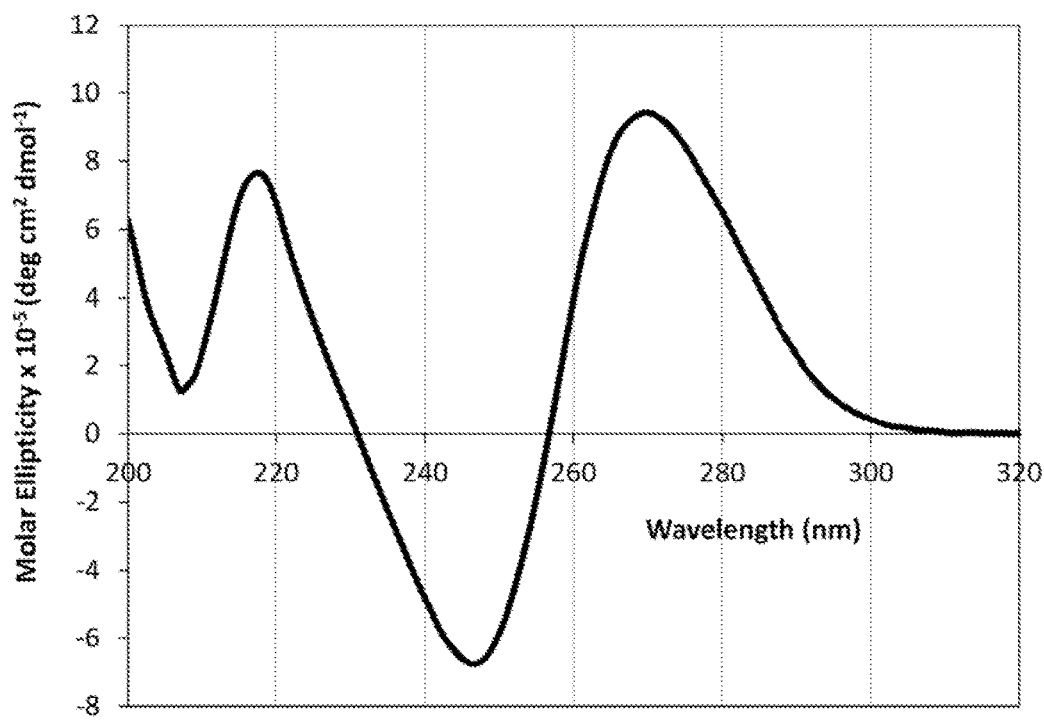
FIG. 10 shows the CD spectrum in water of 20 μM ssDNA-amphiphiles with a 40 nucleotide $G_5$-modified headgroup and no $C_{12}$ spacer.

CD was performed on the 40 nucleotide $G_5$ amphiphiles to probe for the presence of G-quadruplex formation within the headgroups of these amphiphiles. Parallel G-quadruplex structures are tertiary DNA structures formed by the stacking of G-quartet structures, with each G-quartet formed by four guanine nucleotides arranged in a planar, square geometry held together by Hoogsteen hydrogen bonding. These unique structures are stabilized by small cations that fit within the G-quartet structure but can also be formed in pure water (E. W. Choi, et al., *Nucleic Acids Res.*, 2010, 38, 1623-1635) and produce a characteristic CD spectrum with a strong positive peak between 258-265 nm (J. Kypr, et al., *Nucleic Acids Res.*, 2009, 37, 1713-1725; D. M. Gray, et al., *Chirality*, 2008, 20, 431-440). With only five guanines a single headgroup could not form a G-quadruplex with itself but it could form an intermolecular parallel G-quadruplex by interacting with three adjacent headgroups (A. Rajendran, et al., *Nucleic Acids Res.*, 2013, 41, 8738-8747). However, contrary to the hypothesis, the CD spectrum of the 40 nucleotide $G_5$ amphiphiles had a maximum at 270 nm, suggesting that there were not significant G-quadruplex interactions occurring between the amphiphiles' headgroups (FIG. 10).

Figure 11:
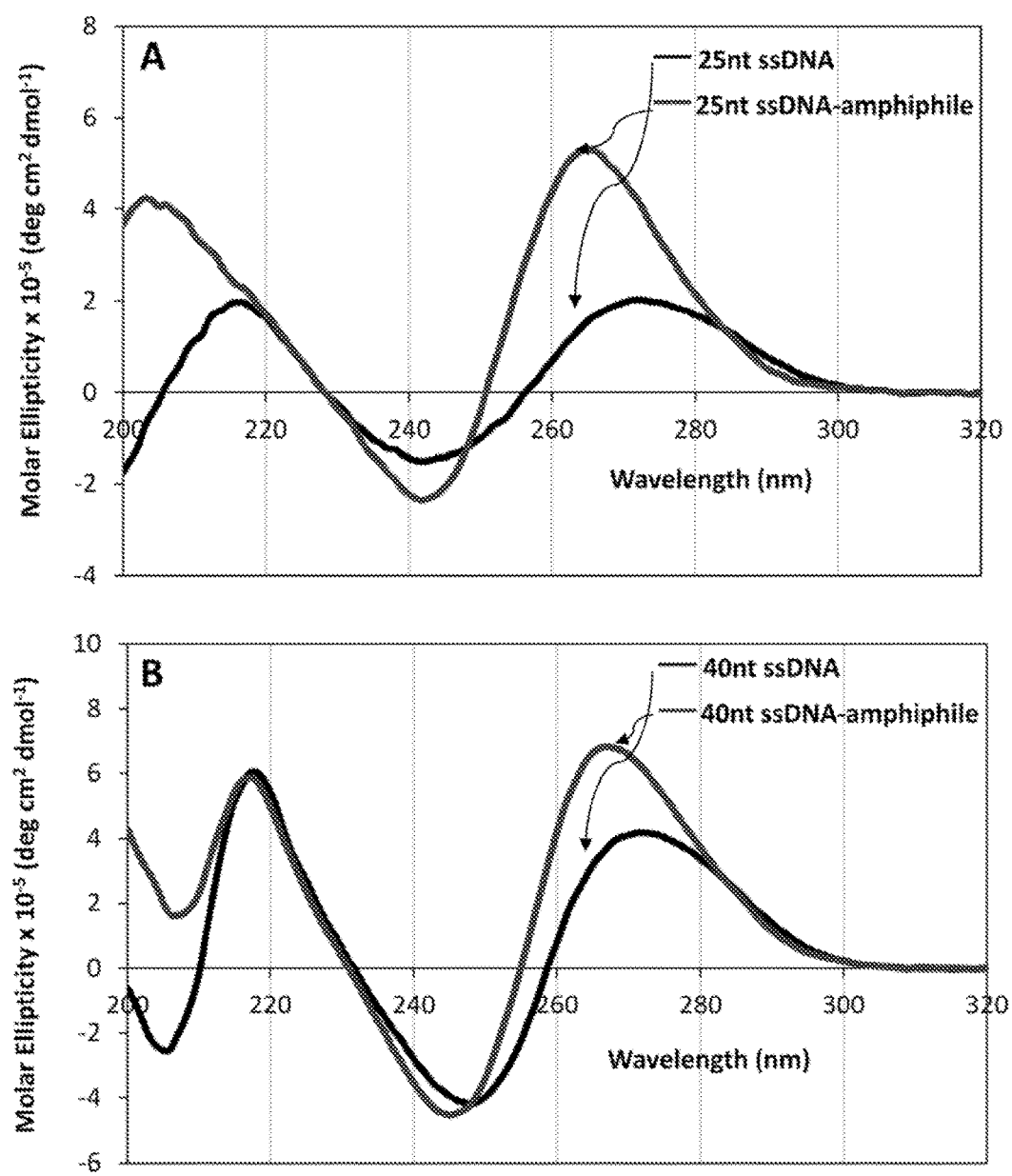
FIGS. 11A-11B shows the CD spectra in water of 20 μM samples with 11A) 25 nucleotide $(GGGT)_3$-modified ('$(GGGT)_3$' disclosed as SEQ ID NO: 1) and 11B) 40 nucleotide $(GGGT)_3$-modified sequences ('$(GGGT)_3$' disclosed as SEQ ID NO: 1) measured as free ssDNA or as ssDNA-amphiphiles without a $C_{12}$ spacer.
Figure 12:
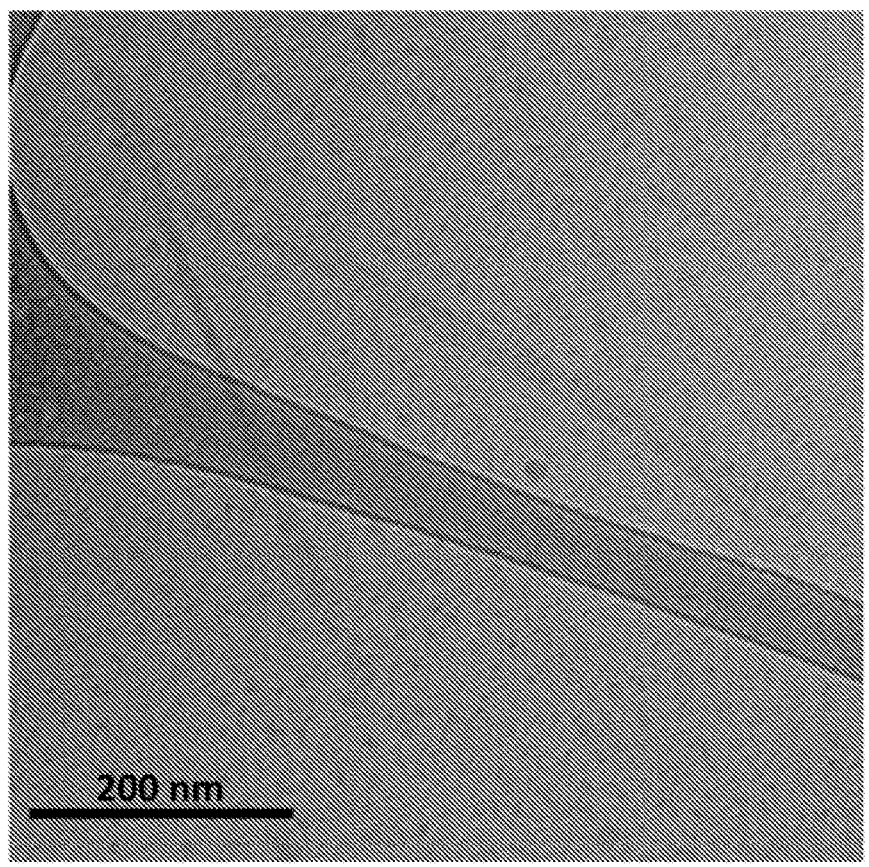
FIG. 12 shows the cryo-TEM image of nanotapes formed by amphiphiles with 25 nucleotide $(GGGT)_3$-modified headgroups ('$(GGGT)_3$' disclosed as SEQ ID NO: 1) and without the $C_{12}$ spacer.

In order to enhance the probability that the ssDNA headgroups would form parallel G-quadruplexes and to test the effect of G-quadruplex interaction on the self-assembly of ssDNA-amphiphiles, two additional headgroups were created from the random guanine-free 25 and 40 nucleotide headgroups. These headgroups had the first 12 nucleotides of the original sequences replaced with the sequence $(GGGT)_3$(SEQ ID NO: 1), as shown in FIG. 1, which is capable of inducing intermolecular G-quadruplexes (B. Waybrant, et al., *Langmuir*, 2014, DOI: 10.1021/la500403v). The CD spectra of the 25 and 40 nucleotide $(GGGT)_3$-modified ssDNA sequences ('$(GGGT)_3$' disclosed as SEQ ID NO: 1) (FIG. 11) measured prior to conjugation to the hydrophobic tails showed a maximum at 272 nm for each length, which can be attributed to a stem-loop secondary structure that typically has a maximum between 275 and 285 nm (J. Kypr, et al., *Nucleic Acids Res.*, 2009, 37, 1713-1725). Following conjugation to the hydrophobic tails and subsequent self-assembly the maxima in the CD spectra of both sequences were substantially shifted, occurring near 265 nm (FIG. 11), which is characteristic of parallel G-quadruplex structures. Cryo-TEM imaging of these two samples showed that both the 25 and 40 nucleotide $(GGGT)_3$ (SEQ ID NO: 1) headgroup amphiphiles formed twisted nanotapes as well as micelles (FIG. 12), although the nanotapes were observed very rarely and did not twist with a consistent periodicity. Thus, the presence of the $(GGGT)_3$ sequence (SEQ ID NO: 1) in the 25 and 40 nucleotide sequences was able to induce the formation of G-quadruplexes between the headgroups of the amphiphiles and produce bilayer twisted nanotape structures in the absence of the $C_{12}$ spacer but was not observed to produce helical nanotapes or nanotubes (Table 1).

Figure 3:
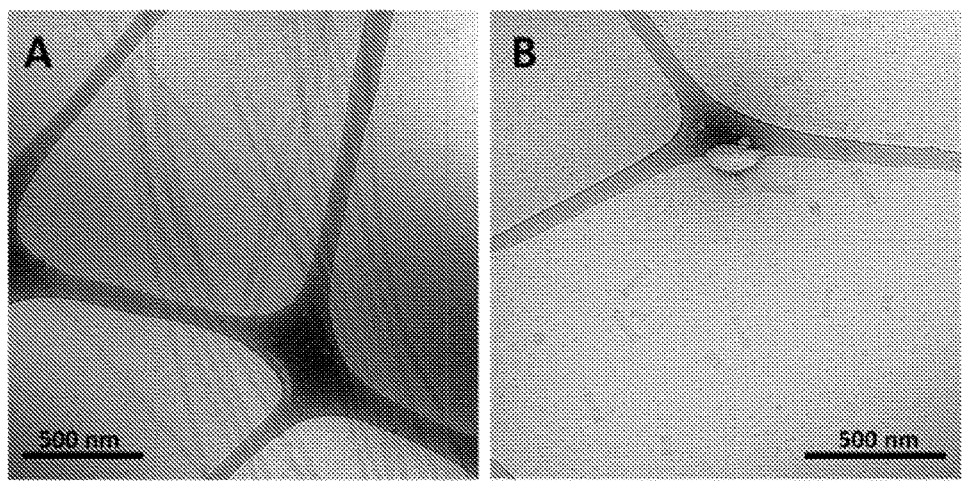
FIGS. 3A-3B show cryo-TEM images of ssDNA nanotubes formed from the self-assembly of amphiphiles with a $C_{12}$ spacer and (3A) 10 nt-1 NoG and (3B) 10 nt-1 $G_5$ headgroups.

Self-assembly of ssDNA-amphiphiles with $G_5$-modified headgroups and a $C_{12}$ spacer Another test of the influence of the guanine-modification of the headgroups, amphiphiles that contained both the $G_5$-modified headgroups and the $C_{12}$ spacers were created and their assembly was compared to that of the amphiphiles with the $C_{12}$ spacer but NoG headgroups. There were no apparent differences in the assembly behaviour of amphiphiles containing the $G_5$ and the NoG headgroups with 25 and 40 nucleotides, as each formed twisted and helical nanotapes and nanotubes. However, there was a dramatic difference in the nanotubes formed by the amphiphiles with headgroups containing only 10 nucleotides. Both amphiphile samples produced nanotubes with similar average diameters (NoG: 29.0±3.6 nm; $G_5$: 32.5±1.3 nm), but amphiphiles with the NoG headgroup produced nanotubes that were microns in length while amphiphiles formed with the $G_5$ headgroup produced nanotubes that were nearly two orders of magnitude shorter and varied between 60 and 350 nm (FIG. 3).

Figure 4:
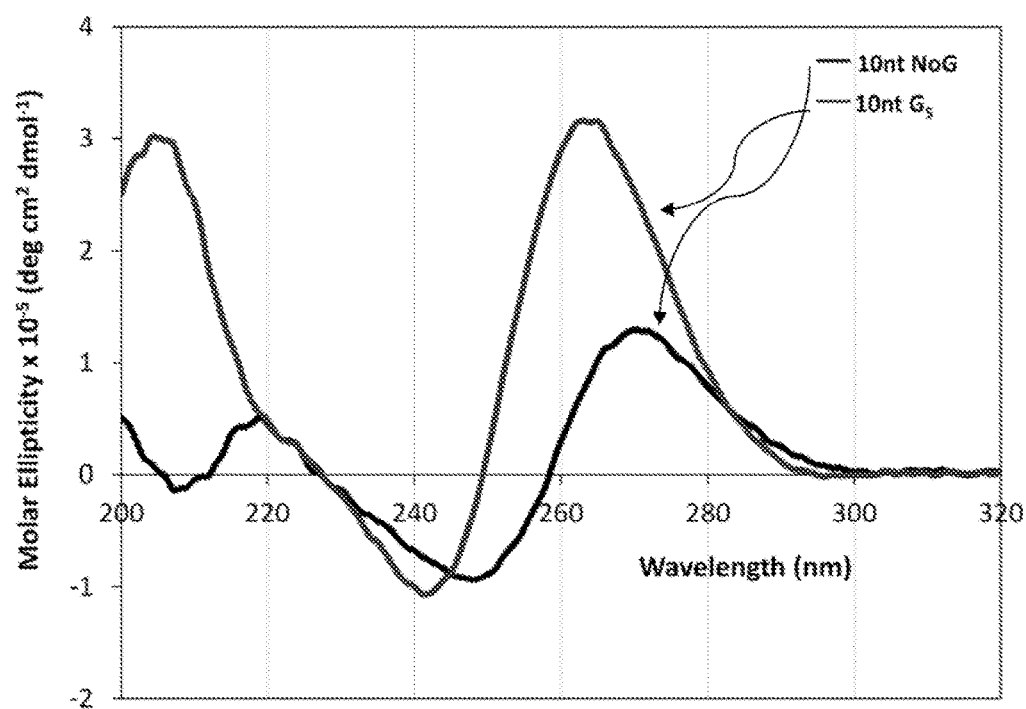
FIG. 4 shows the CD spectra in water of 20 µM ssDNA-amphiphiles with a $C_{12}$ spacer and 10 nucleotide (10 nt-1) NoG or $G_5$ headgroups.
Figure 13:
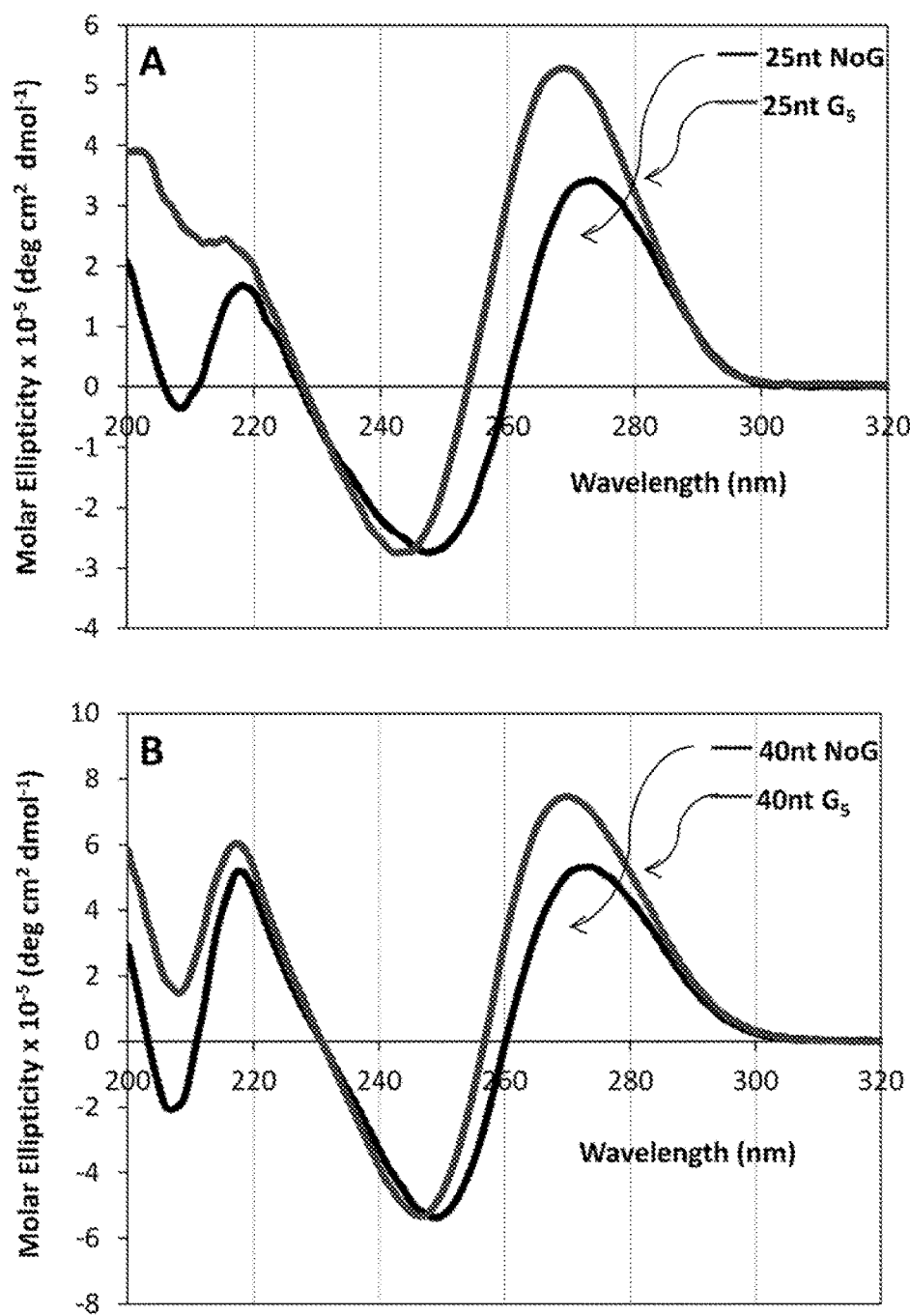
FIGS. 13A-13B shows the CD spectra in water of 20 μMssDNA-amphiphiles with 13A) 25 and 13B) 40 nucleotide NoG or $G_5$ headgroups and with a $C_{12}$ spacer.

CD was performed on the amphiphiles with $C_{12}$ spacers for each length of headgroup to determine the effect of the $G_5$ sequence on the secondary structure of the ssDNA headgroup. The CD spectra of the amphiphiles with the $C_{12}$ spacer and $G_5$-modified headgroups with 25 and 40 nucleotides had maxima near 270 nm (FIG. 13), which is not suggestive of G-quadruplex structure. For comparison, FIG. 13 also includes the CD spectra of the amphiphiles with a $C_{12}$ spacer containing the NoG 25 and 40 nucleotide headgroups and shows that the amphiphiles had maxima at 273 nm, indicative of stem-loop structures. The spectra of the amphiphiles with the $C_{12}$ spacer and the $G_5$-modified 10 nucleotide headgroup had a maximum at 263 nm, which is characteristic of a parallel G-quadruplex structure, while the amphiphiles with 10 nucleotide NoG headgroup produced a CD spectrum with a maximum at 270 nm (FIG. 4). This suggested that of all of the amphiphiles formed with a $C_{12}$ spacer and a $G_5$-modified headgroup only amphiphiles with the 10 nucleotide headgroup formed G-quadruplex secondary structures.

Transitions between twisted nanotapes, helical nanotapes and nanotubes

Figure 5:
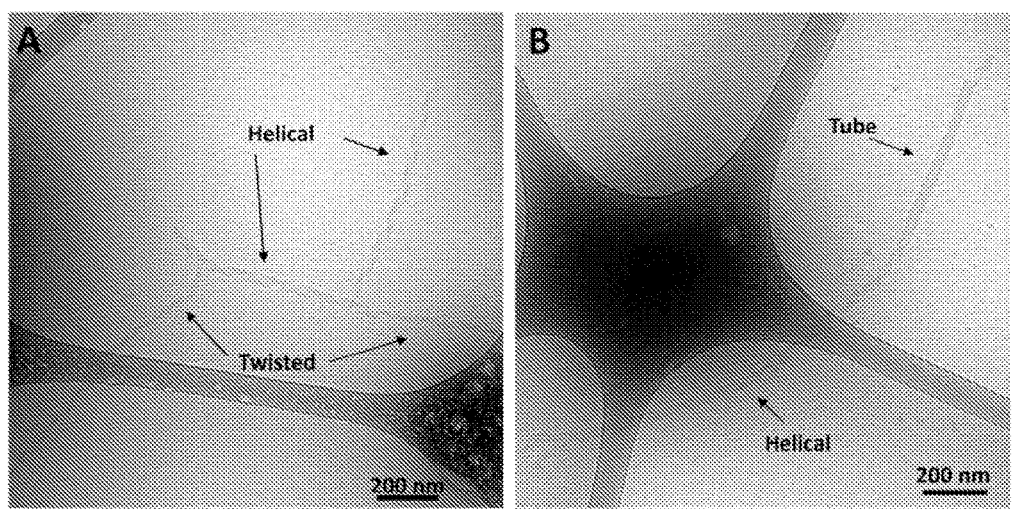
FIGS. 5A-5B show the Cryo-TEM images of ssDNA-amphiphiles formed by NoG headgroups and $C_{12}$ spacers undergoing transitions from 5A) twisted nanotapes to helical nanotapes and 5B) a helical nanotape to a nanotube.
Figure 8:
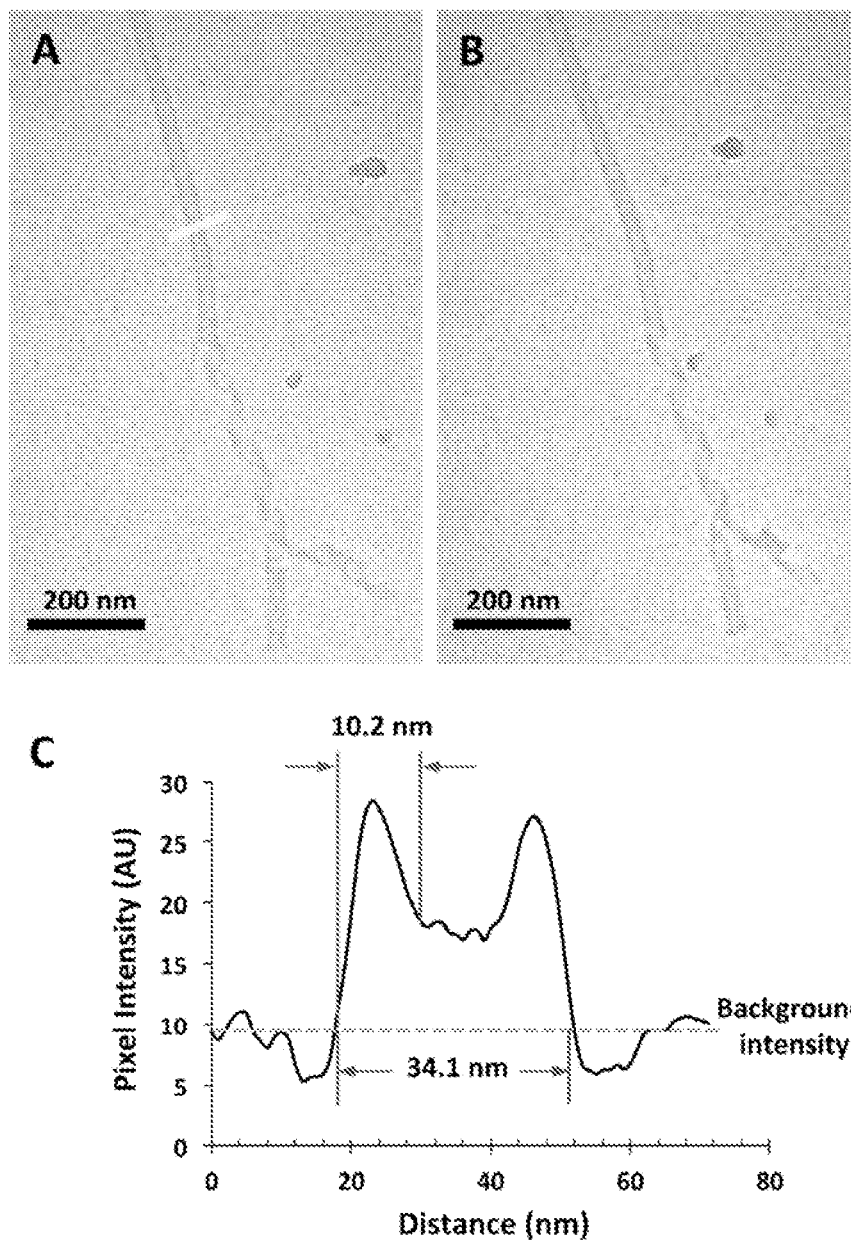
FIGS. 8A-8C shows the cryo-TEM and line-scan analysis of ssDNA-amphiphiles with a 25 nucleotide NoG headgroup and a $C_{12}$ spacer. Images of the same nanotube and helical nanotape section before (3A) and after (3B) a 45° stage tilt. The diameter of the nanotube segment at 0° and 45° tilt is 34.1 nm. 3C) Shows the line-scan analysis of a segment of the untilted cryo-TEM image (line in A) shows the characteristic shape of a hollow cylinder, confirming nanotube formation with 34 nm diameter and 10 nm thick walls.

Cryo-TEM images of the ssDNA-amphiphile nanostructures showed twisted nanotapes, helical nanotapes and nanotubes and also captured the transition from twisted to helical nanotape as well as from helical nanotape to nanotube (FIG. 5, FIG. 8). These images provided direct evidence that the ssDNA-amphiphile nanostructures underwent transitions between these structures in a similar manner as observed in other types of amphiphilic molecules as discussed in detail in the discussion section. Analysis of cryo-TEM images that captured the transition from twisted nanotapes into helical nanotapes showed that the twisted nanotape segments had widths that were substantially smaller than the helical nanotape segments (24±2 versus 38±4 nm) but pitch lengths that were similar (132±6 nm for the twisted nanotapes and 129±7 nm for the helical nanotapes).

Discussion

Figure 6:
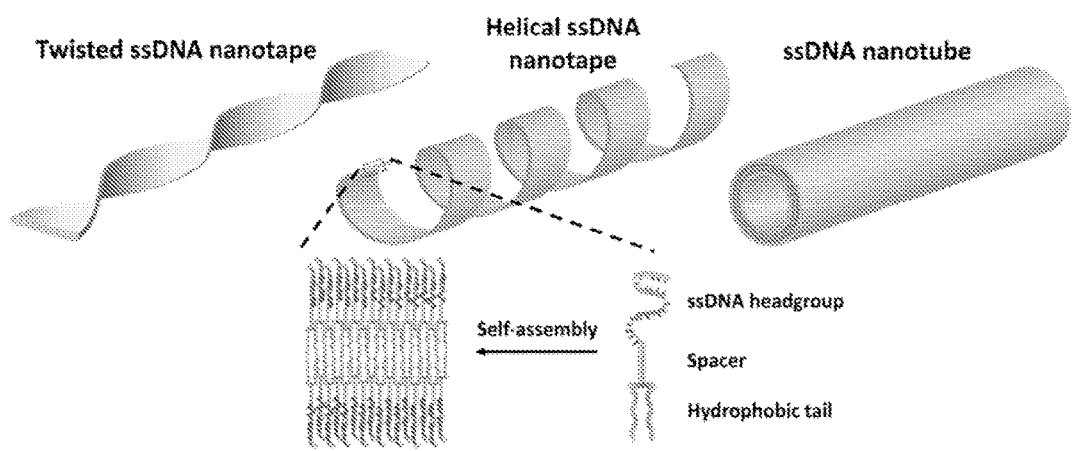
FIG. 6 illustrates a rendering of the self-assembly of ssDNA-amphiphiles into an ordered bilayer structure and the twisted and helical nanotapes and nanotubes that they form. The amphiphile contains three building blocks: a hydrophobic tail, a spacer, and a hydrophilic headgroup (the secondary structure of the headgroup is not shown).

Three building blocks were used to create ssDNA-amphiphiles: a hydrophobic tail (hydrophobic group), a hydrophilic ssDNA headgroup, and a spacer molecule that links the tail and the headgroup. The major driving force for the assembly of the ssDNA-amphiphiles is the hydrophobic force provided by the dialkyl tails. Previous studies have found that the inclusion of a hydrophobic spacer is important for the assembly of the ssDNA-amphiphiles into flat or twisted nanotapes (T. R. Pearce, et al., *Chem. Commun.*, 2014, 50, 210-212; B. Waybrant, et al., *Langmuir*, 2014, DOI: 10.1021/la500403v). Efforts described herein studied the influence of the headgroup length on the self-assembly behaviour of ssDNA-amphiphiles created with the same dialkyl $C_{16}$ tails and $C_{12}$ spacers. Data provided herein demonstrated that ssDNA-amphiphiles with $C_{12}$ spacers and NoG headgroups of 10, 25, or 40 nucleotides not only produced the twisted nanotapes previously seen, but also helical nanotapes and nanotubes. Each of these structures is formed from bilayers of amphiphiles and the hydrophobic tails organized into an interior core with the ssDNA headgroups forming an exterior shell (FIG. 6).

Similar nanotape and nanotube structures have been observed in solutions of different amphiphilic molecules including glycolipids, peptide-amphiphiles, and bolaamphiphiles (A. S. Cuvier, et al., *Soft Matter*, 2014, 10, 3950-3959; E. T. Pashuck et al., *J. Am. Chem. Soc.*, 2010, 132, 8819-8821, H. Shao, et al., *Angew. Chem. Int. Ed.*, 2010, 49, 7688-7691, A. Sorrenti, et al., *Chem. Soc. Rev.*, 2013, 42, 8200-8219). In each case the nanotape and nanotube structures were created from bilayers of amphiphiles, with the hydrophobic moieties sequestered into an inner layer and surrounded with the hydrophilic headgroups to form the exterior of the nanostructure. The chirality of the individual amphiphile requires that the amphiphiles organize with their neighbouring molecules at non-zero angles, generating a preferred orientation of each amphiphile tail and headgroup within the self-assembled bilayer, which induces twisting (A. Sorrenti, et al., *Chem. Soc. Rev.*, 2013, 42, 8200-8219). The ssDNA-amphiphiles described herein are rich in chirality, with chiral centers in the hydrophobic tails as well as the nucleotides of the ssDNA headgroups. As such, it is possible that the chirality of the individual ssDNA-amphiphile is responsible for producing the twisting that was observed in the ssDNA-amphiphile nanotapes.

The ability for self-assembled structures to transition from a twisted nanotape morphology to a helical nanotape morphology has been captured and described in a number of publications (E. T. Pashuck et al., *J. Am. Chem. Soc.*, 2010, 132, 8819-8821; A. Sorrenti, et al., *Chem. Soc. Rev.*, 2013, 42, 8200-8219; L. Ziserman, et al., *J. Am. Chem. Soc.*, 2011, 133, 2511-2517; L. Ziserman, et al., *Phys. Rev. Lett*, 2011, 106, 238105, Z. Chen, et al., *Appl. Phys. Lett.*, 2011, 98, 011906, A. Perino, et al., *Langmuir*, 2011, 27, 12149-12155). For example, a peptide-amphiphile that contained three phenylalanine residues that were capable of intermolecular π-π stacking was observed to form short twisted bilayer nanotapes 30 sec after dissolution in water (E. T. Pashuck et al., *J. Am. Chem. Soc.*, 2010, 132, 8819-8821). These short structures grew into long twisted nanotapes within ten minutes, that coexisted with helical tapes after two weeks and transitioned entirely to helical tapes after four weeks. Similarly, single amino acid amphiphiles dissolved in water were found to form twisted nanotapes after 24 h, a mixture of twisted and helical nanotapes after one week, which were almost entirely helical after four weeks, and finally transitioned into nanotubes between one and four months L. (Ziserman, et al., *J. Am. Chem. Soc.*, 2011, 133, 2511-2517).

These and other reports propose that the transition from a twisted to helical bilayer nanotape morphology requires a change in membrane curvature from Gaussian (saddle-like) to cylindrical, an event that is often attributed to a rearrangement of the individual amphiphiles into a molecular organization that is more ordered or crystalline (E. T. Pashuck et al., *J. Am. Chem. Soc.*, 2010, 132, 8819-8821, H. Shao, et al., *Angew. Chem. Int. Ed.*, 2010, 49, 7688-7691, J. V. Selinger, et al., *J. Phys. Chem. B*, 2001, 105, 7157-7169, M. S. Spector, et al., *Nano Lett.*, 2001, 1, 375-378).[18,19,25,26] The forces that are often identified as causing the order or crystallinity are hydrogen-bonding and π-π stacking between individual amphiphiles although electrostatic and hydrophobic forces are also likely important (E. T. Pashuck et al., *J. Am. Chem. Soc.*, 2010, 132, 8819-8821; L. Ziserman, et al., *J. Am. Chem. Soc.*, 2011, 133, 2511-2517). The $C_{12}$ spacer has previously been found to play an important role in producing the bilayer nanotapes, possibly by forcing the aptamer headgroups into close proximity of each other, thus reducing their interfacial headgroup area, which allows the nanotapes to form (T. R. Pearce, et al., *Chem. Commun.*, 2014, 50, 210-212; B. Waybrant, et al., *Langmuir*, 2014, DOI: 10.1021/la500403v). The $C_{12}$ spacer may also be helping to ensure that the amphiphiles can organize into crystalline or well-ordered bilayers by extending the large ssDNA headgroups away from the interface and relieving some of the electrostatic or steric constraints that could impede close and ordered packing of the amphiphiles. This may be especially important in the case of the NoG headgroups that do not appear to interact with each other.

Hydrogen bonding can occur between guanine nucleobases and produce the G-quartet structures that can stack into G-quadruplexes. For this reason it was investigated whether guanine-rich headgroups that can form parallel G-quadruplexes could be used in place of the $C_{12}$ spacer to produce nanotapes and nanotubes. Amphiphiles with the $(GGGT)_3$ (SEQ ID NO: 1) headgroups 25 and 40 nucleotides in length and without the $C_{12}$ spacer were found to assemble into twisted nanotapes but did not appear to progress into helical nanotapes or nanotubes while amphiphiles without either the $(GGGT)_3$ sequence (SEQ ID NO: 1) or the $C_{12}$ spacer formed only micelles. This result suggests that the additional force produced by the hydrogen bonding of the parallel G-quadruplex structure was important to the formation of the bilayer nanotape structure but was unable to induce the change in membrane curvature required to transition into helical nanotapes and nanotubes.

The literature offers insight into the transition from twisted to helical nanotapes and from helical nanotapes to nanotubes. Recent theoretical and experimental work shows that the width of the nanotape is a critical parameter in determining the morphology of the nanotape (L. Ziserman, et al., *J. Am. Chem. Soc.*, 2011, 133, 2511-2517; L. Ziserman, et al., *Phys. Rev. Lett.*, 2011, 106, 238105; S. Armon, et al., *Soft Matter*, 2014, 10, 2733-2740). Specifically, as the bilayer grows in width it becomes energetically favorable for the bilayer to transition from Gaussian to cylindrical curvature, thus producing the transition from a twisted to helical morphology. Theoretical studies also pointed out that shape selection in self-assembled chiral molecules may involve a geometrical frustration, and thus a competition between bending and stretching (S. Armon, et al., *Soft Matter*, 2014, 10, 2733-2740; R. Ghafouri, et al., *Phys. Rev. Lett.*, 2005, 94, 138101). The transition from twisted to helical ribbons (or nanotapes) to nanotubes has been described by two competing theories: a "closing-pitch model" and a "growing width model" (T. Shimizu, et al., *Chem. Rev.*, 2005, 105, 1401-1443). The closing-pitch model assumes that a helical nanotape maintains its width while the pitch shortens until the edges of the nanotape meet to form a nanotube while the growing width model assumes the pitch remains constant and the nanotape widens until a closed nanotube is formed. An alternate possibility is that some of the twisted and helical nanotapes are at equilibrium and never transition into nanotubes as observed previously in other amphiphilic systems.[30]

Analysis of cryo-TEM images that captured the transition from twisted nanotapes into helical nanotapes, like those shown in FIG. 5, showed that the twisted nanotape segments had widths that were substantially smaller than the helical nanotape segments. This suggests that the transition from twisted to helical nanotape occurs as the width of the nanotape increases and that the "growing width" model rather than the "shortening pitch" model best describes the mechanism of transitioning from twisted to helical nanotapes as well as nanotube formation. Furthermore, based on the observed transitions between twisted nanotapes and helical nanotapes, and helical nanotape and nanotubes, it appears that the twisted and helical nanotapes may be metastable morphologies that could be progressing into nanotubes. While the transition from twisted nanotapes to nanotubes was found to occur over weeks in many other amphiphile systems (E. T. Pashuck et al., *J. Am. Chem. Soc.*, 2010, 132, 8819-8821; L. Ziserman, et al., *J. Am. Chem. Soc.*, 2011, 133, 2511-2517; J. Adamcik, et al., *Angew. Chem. Int. Ed.*, 2011, 50, 5495-5498), the ssDNA-amphiphiles described herein were observed to form nanotubes within 30 min after dissolution in water, suggesting they rapidly transition from nanotapes to nanotubes. It is unclear if every nanotape structure is undergoing a transition toward the nanotube morphology as nanotapes were found to persist in solution after seven days of aging. However, in light of the longer times required for other amphiphilic self-assemblies to transition into helical nanotapes and nanotubes, the seven days of aging described herein may be insufficient to draw conclusions regarding the kinetics of ssDNA-amphiphile assembly.

Conclusion ssDNA-amphiphiles containing a random nucleic acid headgroup can adopt a variety of self-assembled structures including twisted and helical bilayer nanotapes and nanotubes. These structures are substantially more complex than spherical and cylindrical micelles observed by others in the literature. The ability to create DNA nanotubes from ssDNA-amphiphiles is particularly important, as nanotubes have been utilized for targeted drug delivery of small molecules and siRNA, as templates for nanowires and as tracks for molecular motors. For many of these applications there is no need for the complex designs made possible by other DNA nanotechnology approaches that rely entirely on DNA base pairing. ssDNA-amphiphile assembly into nanotubes occurs rapidly via the association of the hydrophobic tails and does not require stringent annealing conditions as demonstrated by the nanotube formation minutes after amphiphile dissolution in water. Furthermore, DNA nanotubes were formed using ssDNA sequences of different lengths and nucleic acid sequences, and the addition of a guanine-rich sequence in the headgroup was found to be capable of modifying the assembly, all of which demonstrate the versatility of the amphiphile-based self-assembly strategy for forming DNA nanostructures.

EXAMPLE 2

Amphiphiles (compounds 2A-2D and 3A) that contain G-enriched and C-enriched ssDNA sequences were prepared in the manner described in Example 1 and are shown in Scheme 4 and Scheme 5. These compounds all formed nanotubes.

Scheme 4 (Compounds 1E and 2A-2D with spacer)

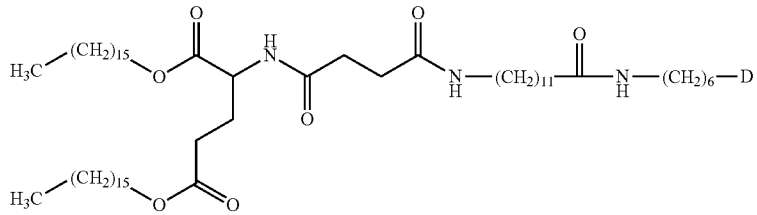

Compound number: value for D (observed ms)

```
Compound 1E: D =
                                              (SEQ ID NO: 3)
5'-GGGGGTTCTC-3' (4128.3)

Compound 2A: D =
                                              (SEQ ID NO: 13)
5'-GGGTGGGTGGGTGGGTCATCTATTA-3' (8896.0)

Compound 2B: D =
                                              (SEQ ID NO: 14)
5'-GGTGGTGGTGGTATTTCATCTATTA-3' (8803.3)

Compound 2C: D =
                                              (SEQ ID NO: 15)
5'-GGGTGGGTGGGTGGGTCATCTATTAAACCACCAATTAATT-3'
(13461.0)

Compound 2D: D =
                                              (SEQ ID NO: 16)
5'-CCCTATTCCCAGATCCCATTACCC-3' (8185.0).
```

Scheme 5 (Compound 3A without spacer)

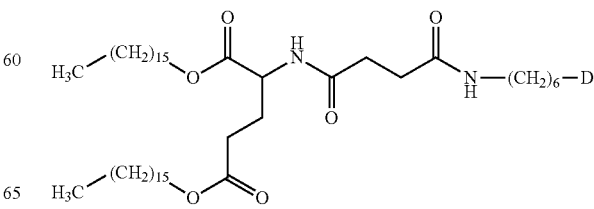

Compound number: value for D (observed ms)

```
Compound 3A: D =
                                         (SEQ ID NO: 16)
5'-CCCTATTCCCAGATCCCATTACCC-3'  (7987.5)
```

It has been discovered that amphiphiles that contain G-enriched (which G sequences can from G-quadruplexes) and C-enriched (which C sequences can from i-motifs) ssDNA sequences promote the formation of nanotubes including shorter nanotubes. It has also been discovered that G-enriched and C-enriched ssDNA sequences can form nanotubes and nanotapes in the absence of a spacer (i.e., in the absence of moiety B of the compounds of formula I).

In one embodiment D comprises greater than 5% G nucleotides. In one embodiment D comprises greater than 8% G nucleotides. In one embodiment D comprises greater than 10% G nucleotides. In one embodiment D comprises greater than 30% G nucleotides. In one embodiment D comprises greater than 40% G nucleotides. In one embodiment D comprises greater than 50 G nucleotides. In one embodiment D comprises greater than 60% G nucleotides.

In one embodiment D comprises greater than 5% C nucleotides. In one embodiment D comprises greater than 8% C nucleotides. In one embodiment C comprises greater than 10% G nucleotides. In one embodiment C comprises greater than 30% G nucleotides. In one embodiment D comprises greater than 40% G nucleotides. In one embodiment C comprises greater than 50% G nucleotides. In one embodiment D comprises greater than 60% G nucleotides.

EXAMPLE 3

An amphiphile (compound 4A) that contains a longer hydrophobic (lipophilic) group or tail (e.g., hydrocarbon chain) was prepared in the manner described in Example 1 and is shown in Scheme 6. Nanotubes prepared from compound 4A appear to have a greater diameter than the corresponding compound that has a 16 carbon hydrophobic group as demonstrated by TEMs (room temperature). Thus, varying the hydrophobic group of the amphiphiles may be a viable method to control the diameter of the resultant nanotubes.

Scheme 6 (compound 4A).

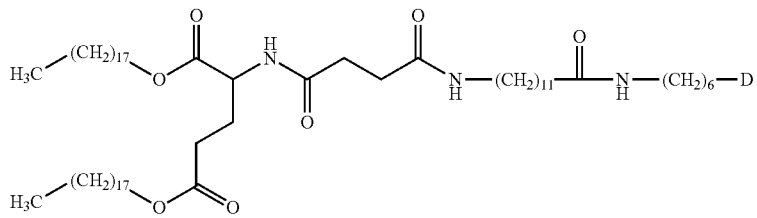

Compound number: value for D (observed ms)

```
Compound 4A: D =
                                    (SEQ ID NO: 3)

5'-GGGGGTTCTC-3'  (4185.3)
```

EXAMPLE 4

Amphiphiles (compounds 5A-5B; shown in Scheme 8) that contain a different hydrophobic (lipophilic) group or tail (e.g., hydrocarbon chain) were prepared as described in Scheme 7.

Scheme 7

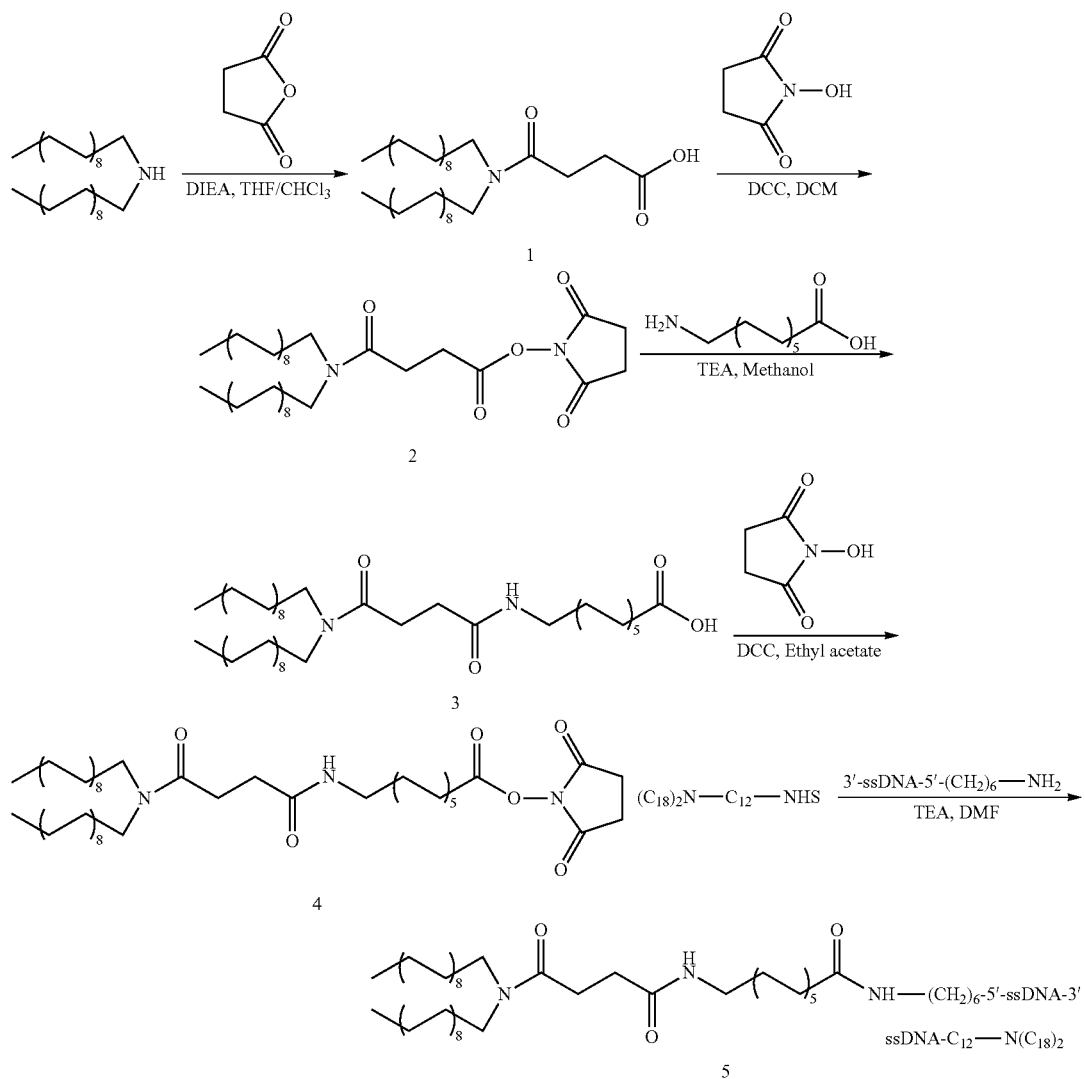

First dioctadecylamine was dissolved in CHCl$_3$/THF (50%/50%, v/v) at 50° C. Then 15% molar excess of succinic anhydride and 50% molar excess of N,N-diisopropylethylamine (DIEA) were added. After 6 h, the solvents were evaporated and the product 1 was recrystallized from ethyl acetate. Then N-hydroxysuccinimide (NHS, 1.5× molar excess) was added to a solution of 1 in dichloromethane (DCM) at room temperature. After cooling to 0° C., N,N'-dicyclohexylcarbodiimide (DCC, 2× molar excess) was added. The solution was stirred for 1 h at 0° C. and then overnight at room temperature. The precipitated dicyclohexyl urea (DCU) was filtered off and the solvent was removed in vacuum. The product 2 was recrystallized from ethyl acetate. The NHS-activated 3 was then reacted with excess spacer, for example C$_{12}$, (1.5× molar excess) in methanol for 6 hr at 50° C. Then methanol was removed and DCM was added to dissolve the product 3. The excess spacer (didn't dissolve in DCM) was removed by filtration. DCM was then evaporated and the product 3 was recrystallized from ethyl acetate. As a last step, 3 was activated by NHS to obtain the product 4 ((C$_{18}$)$_2$-C$_{12}$-NHS). The conjugation of the ssDNA to 4 is similar to the synthesis of the ssDNA-amphiphiles with glutamic acid. The product 5 was purified by RP-HPLC.

Scheme 8

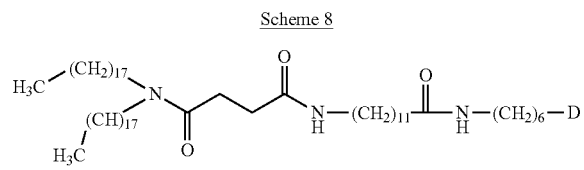

Compound number: value for D (observed ms)

```
Compound 5A: D =
                                        (SEQ ID NO: 3)
5'-GGGGGTTCTC-3'  (Mass Spec: 4054.6)
```

```
Compound 5B: D =
                                             (SEQ ID NO: 4)
    5'-TTCTATTCTC-3'  (Mass Spec: 3925.3)
```

All publications, patents and patent applications cited herein are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A self-assembled nanotube comprising a nucleic acid amphiphile of formula I:

A-B-C-D    I wherein:

A has the formula:

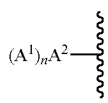

wherein:

each $A^1$ is independently a saturated or unsaturated ($C_5$-$C_{30}$) hydrocarbon chain;

$A^2$ is a saturated or unsaturated ($C_5$-$C_{25}$) hydrocarbon chain wherein one or more of the carbon atoms of the hydrocarbon chain is replaced independently with an —O—, —S—, N or —NR— group and wherein one or more of the carbon atoms of the hydrocarbon chain is optionally substituted independently with an oxo or thioxo group, and wherein each R is independently an H, saturated ($C_1$-$C_{10}$) hydrocarbon chain or unsaturated ($C_2$-$C_{10}$) hydrocarbon chain; and n is 1, 2, 3 or 4;

B is a saturated or unsaturated ($C_{10}$-$C_{16}$) hydrocarbon chain wherein 1 or 2 of the carbon atoms of the hydrocarbon chain is replaced independently with an —O—, —S or —NR— group and wherein 1 or 2 of the carbon atoms of the hydrocarbon chain is optionally substituted independently with an oxo or thioxo group, and wherein each R is independently H, saturated ($C_1$-$C_{10}$) hydrocarbon chain or unsaturated ($C_2$-$C_{10}$) hydrocarbon chain, or B is absent provided that when B is absent, the polynucleotide comprises one or more guanine nucleotides and is greater than 10 nucleotides in length;

C is absent, or C is a saturated or unsaturated ($C_2$-$C_{10}$) hydrocarbon chain; and D is single stranded DNA comprising 5-50 nucleotides or a single stranded RNA comprising 5-50 nucleotides;

or a salt thereof; and provided that D is not the nucleotide sequence (SEQ ID NO: 2)
GGGGTGGGTGGGGGGCACGTGTGGGGGCGGCCAGGGTGCT.

2. The nanotube of claim 1, wherein each $A^1$ is independently a saturated or unsaturated ($C_{10}$-$C_{30}$) hydrocarbon chain.

3. The nanotube of claim 1 wherein A is

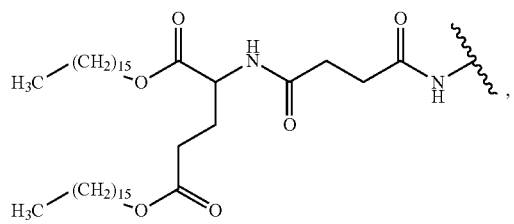

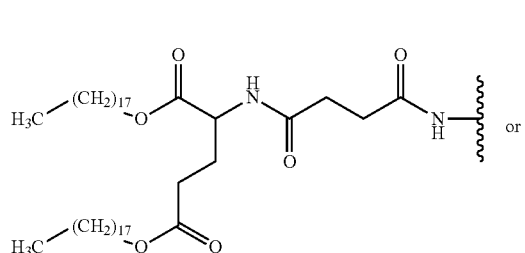

4. The nanotube of claim 1, wherein B is a saturated or unsaturated ($C_{10}$-$C_{16}$) hydrocarbon chain wherein 1 or 2 of the carbon atoms of the hydrocarbon chain are replaced independently with an —O—, —S or —NR— group and wherein 1 or 2 of the carbon atoms of the hydrocarbon chain are substituted independently with an oxo or thioxo group, and wherein each R is independently H, saturated ($C_1$-$C_{10}$) hydrocarbon chain or unsaturated ($C_2$-$C_{10}$) hydrocarbon chain.

5. The nanotube of claim 1, wherein B is

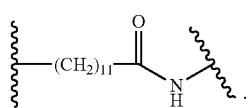

6. The nanotube of claim 1 wherein C is a saturated or unsaturated ($C_2$-$C_{10}$)hydrocarbon chain.

7. The nanotube of claim 1, wherein D is selected from the group consisting of:

5'-TTCTATTCTC-3'; (SEQ ID NO: 4)

5'-CCAATTAATT-3'; (SEQ ID NO: 5)

5'-TTCTATTCTCACATTTCATCTATTA-3'; (SEQ ID NO: 6)

5'-TTCTATTCTCACATTTCATCTATTAAACCACCAATTAATT-3'; (SEQ ID NO: 7)

5'-GGGGGTTCTC-3'; (SEQ ID NO: 3)

5'-GGGGGTAATT-3'; (SEQ ID NO: 8)

5'-GGGGGTTCTCACATTTCATCTATTA-3'; (SEQ ID NO: 9)

5'-GGGGGTTCTCACATTTCATCTATTAAACCACCAATTAATT-3'; (SEQ ID NO: 10)

5'-GGGTGGGTGGGTATTTCATCTATTA-3'; (SEQ ID NO: 11)

5'-GGGTGGGTGGGTATTTCATCTATTAAACCACCAATTAATT-3'; (SEQ ID NO: 12)

5'-GGGTGGGTGGGTGGGTCATCTATTA-3'; (SEQ ID NO: 13)

5'-GGTGGTGGTGGTATTTCATCTATTA-3'; (SEQ ID NO: 14)

5'-GGGTGGGTGGGTGGGTCATCTATTAAACCACCAATTAATT-3' and (SEQ ID NO: 15)

5'-CCCTATTCCCAGATCCCATTACCC-3'. (SEQ ID NO: 16)

8. A pharmaceutical composition comprising a nanotube as described in claim 1 or a pharmaceutically acceptable salt thereof and a pharmaceuticaly acceptable carrier.

9. The nanotube of claim 1 wherein $A^2$ is a saturated ($C_{10}$-$C_{20}$) hydrocarbon chain wherein 1, 2, 3, 4, 5, 6, 7 or 8 of the carbon atoms of the hydrocarbon chain is replaced independently with an —O—, —S—, N or —NR— group and wherein 1, 2, 3, 4, 5, 6, 7 or 8 of the carbon atoms of the hydrocarbon chain is substituted independently with an oxo or thioxo group, and wherein each R is independently an H, saturated ($C_1$-$C_{10}$) hydrocarbon chain or unsaturated ($C_2$-$C_{10}$) hydrocarbon chain.

10. The nanotube of claim 1 wherein $A^2$ is a saturated ($C_{10}$-$C_{16}$) hydrocarbon wherein 1, 2, 3, 4, 5 or 6 of the carbon atoms of the hydrocarbon chain is replaced independently with an —O—, —S or —NR— group and wherein 1, 2, 3, 4, 5 or 6 of the carbon atoms of the hydrocarbon chain is substituted independently with an oxo or thioxo group, and wherein each R is independently an H, saturated ($C_1$-$C_{10}$) hydrocarbon chain or unsaturated ($C_2$-$C_{10}$) hydrocarbon chain.

11. The nanotube of claim 1 wherein each $A^1$ is independently a saturated ($C_{10}$-$C_{25}$) hydrocarbon chain.

* * * * *

SEQUENCE LISTING

```
<160> NUMBER OF SEQ ID NOS: 16

<210> SEQ ID NO 1
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gggtgggtgg gt                                                             12

<210> SEQ ID NO 2
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ggggtgggtg ggggcacgt gtggggcgg ccagggtgct                                 40

<210> SEQ ID NO 3
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gggggttctc                                                                10

<210> SEQ ID NO 4
<211> LENGTH: 10
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 4
ttctattctc                                                              10

<210> SEQ ID NO 5
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ccaattaatt                                                              10

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ttctattctc acatttcatc tatta                                             25

<210> SEQ ID NO 7
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ttctattctc acatttcatc tattaaacca ccaattaatt                             40

<210> SEQ ID NO 8
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gggggtaatt                                                              10

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gggggttctc acatttcatc tatta                                             25

<210> SEQ ID NO 10
<211> LENGTH: 40
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 10
gggggttctc acatttcatc tattaaacca ccaattaatt     40

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gggtgggtgg gtatttcatc tatta     25

<210> SEQ ID NO 12
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gggtgggtgg gtatttcatc tattaaacca ccaattaatt     40

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gggtgggtgg gtgggtcatc tatta     25

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ggtggtggtg gtatttcatc tatta     25

<210> SEQ ID NO 15
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gggtgggtgg gtgggtcatc tattaaacca ccaattaatt     40

<210> SEQ ID NO 16
<211> LENGTH: 24
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 16
ccctattccc agatcccatt accc                                              24
```